United States Patent [19]

Kalopissis et al.

[11] 4,093,806
[45] June 6, 1978

[54] INDOANILINES

[75] Inventors: Gregoire Kalopissis, Paris; Andree Bugaut, Boulogne-sur-Seine; Francoise Estradier, Paris, all of France

[73] Assignee: L'Oreal, Paris, France

[21] Appl. No.: 798,886

[22] Filed: May 20, 1977

Related U.S. Application Data

[62] Division of Ser. No. 619,477, Oct. 3, 1975, Pat. No. 4,046,786, which is a division of Ser. No. 482,523, Jun. 24, 1974, Pat. No. 3,929,404.

[30] Foreign Application Priority Data

Jun. 22, 1973 Luxembourg ............................ 67860

[51] Int. Cl.$^2$ .......................................... C07D 295/14
[52] U.S. Cl. .................................... 544/165; 544/166; 260/293.74; 260/293.76; 260/293.77; 260/293.79
[58] Field of Search .............................. 544/166, 165; 260/293.74, 293.76, 293.77, 293.79

[56] References Cited

PUBLICATIONS

Kalopissis et al "Chem. Abstracts" vol. 83 (1975) No. 12212x.

*Primary Examiner*—Henry R. Jiles
*Assistant Examiner*—R. W. Ramsuer
*Attorney, Agent, or Firm*—Cushman, Darby & Cushman

[57] ABSTRACT

Indoaniline of the formula

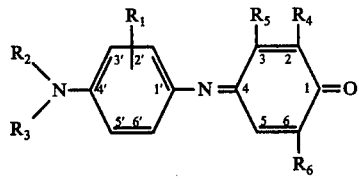

wherein $R_1$ represents hydrogen, halogen, alkyl or alkoxy;

$R_2$ represents alkyl, hydroxyalkyl, carbamylalkyl, piperidinoalkyl, morpholinoalkyl, sulfoalkyl, dialkylaminoalkyl, acylaminoalkyl, (preferably acetylaminoalkyl or benzoylaminoalkyl) and mesylaminoalkyl;

$R_3$ represents hydroxyalkyl, carbamylalkyl, piperidonoalkyl, morpholinoalkyl, sulfoalkyl, dialkylaminoalkyl, acylaminoalkyl, (preferably acetylaminoalkyl or benzoylaminoalkyl), mesylaminoalkyl; or $R_2$ and $R_3$ together form with the nitrogen atom to which they are attached a heterocycle selected from piperidino or morpholino;

$R_4$, $R_5$ and $R_6$ each independently represents hydrogen, halogen, alkyl, alkoxy, acylamino, ureido or carbalkoxyamino, and $R_5$ can also represent amino, alkylamino, hydroxyalkylamino or carbamylalkylamino. The alkyl and alkoxy groups above can contain from 1 to 6 carbon atoms and the acyl group can contain from 2 to 7 carbon atoms. The present invention also relates to a process for the preparation of the above indoanilines and to dye compositions for keratinic fibers, and in particular living human hair, containing said indoanilines.

10 Claims, No Drawings

INDOANILINES

This is a division of Ser. No. 619,477, filed Oct. 3, 1975, now U.S. Pat. No. 4,046,786 which in turn is a division of Ser. No. 482,523, filed June 24, 1974, now U.S. Pat. No. 3,929,404.

The present invention relates to new indoanilines of the formula

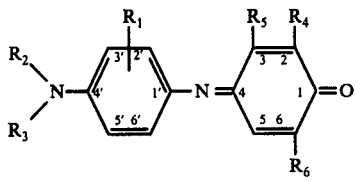

wherein
$R_1$ represents hydrogen, halogen, alkyl or alkoxy;
$R_2$ represents alkyl, hydroxyalkyl, carbamylalkyl, piperidinoalkyl, morpholinoalkyl, sulfoalkyl, dialkylaminoalkyl, acylaminoalkyl, (preferably acetylaminoalkyl or benzoylaminoalkyl) and mesylaminoalkyl;
$R_3$ represents hydroxyalkyl, carbamylalkyl, piperidinoalkyl, morpholinoalkyl, sulfoalkyl, dialkylaminoalkyl, acylaminoalkyl, (preferably acetylaminoalkyl or benzoylaminoalkyl), mesylaminoalkyl; or $R_2$ and $R_3$ together form with the nitrogen atom to which they are attached a heterocycle selected from piperidino or morpholino;
$R_4$, $R_5$ and $R_6$ each independently represents hydrogen, halogen, alkyl, alkoxy, acylamino, ureido or carbalkoxyamino, with the proviso that at least one of $R_4$, $R_5$ and $R_6$ not denoting hydrogen or halogen and at least two of them not denoting hydrogen when $R_4$ or $R_6$ is methyl, and $R_5$ can also represent amino, alkylamino, hydroxyalkylamino or carbamylalkylamino. The alkyl and alkoxy groups above can contain from 1 to 6 carbon atoms and the acyl group can contain from 2 to 7 carbon atoms.

The present invention is also directed to a process for the preparation of the above indoanilines and to dye compositions for keratinic fibers, and in particular living human hair, containing said indoanilines. It will be understood that the above compounds can be present in the tautomeric forms of that represented by formula I.

Among the tautomer forms possible, one can mention

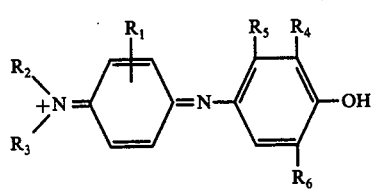

and when $R_5$ represents amino, alkylamino, hydroxyalkylamino or carbamylalkylamino, the formula

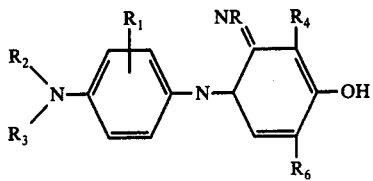

in which $R_1$ to $R_6$ have the meanings indicated above and R represents hydrogen, alkyl, hydroxyalkyl or carbamylalkyl.

The compounds of formula I can be prepared by condensing a compound of the formula

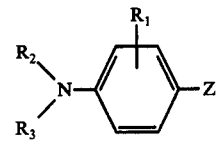

wherein Z designates $NH_2$, or NO when $R_1$ is in position meta to the $-NR_2R_3$ group, on a phenolic compound of the formula

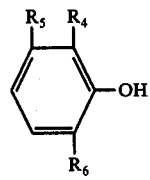

wherein $R_1$, $R_2$, $R_3$, $R_4$, $R_5$, and $R_6$ have the meanings given above, or the meanings given below.

In a first embodiment of a present invention, when Z designates $NH_2$, the phenolic compound of formula III is condensed on a paraphenylenediamine of the formula

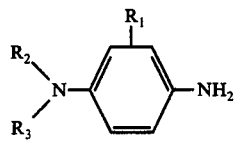

wherein $R_1$, $R_2$, and $R_3$ have the meanings given above in an aqueous alkaline, hydroalcoholic (preferably hydroethanolic or hydroisopropanolic) or hydroacetonic medium having the pH greater than 8 in the presence of an alkalizing agent and an oxidizing agent and at a temperature of about 0° C.

The paraphenylenediamine can also be present in the form of an acid addition salt, for example in the form of a hydrochloride, a hydrobromide, sulfate or phosphate.

The oxidizing agent usefully employed in this condensation reaction can be, for example, $H_2O_2$, an alkaline persulfate such as potassium or ammonium persulfate and an alkaline ferricyanide such as potassium ferricyanide.

The quantity of the oxidizing agent employed can vary from 1-5 times, preferably 1-3 times the stoichiometric amount required for oxidizing the p-phenylenediamine to a quinone diimine.

Representative phenolic compounds usefully employed include 2-ureido phenol, 2,5-xylenol, 2-methyl-5-amino phenol, 2-methyl-5-ureido phenol, 2-methyl-5- acetylaminophenol, 2-chloro-5-amino phenol, 2-chloro-5-acetylamino phenol, 2,6-dimethyl-3-acetylamino phenol, 2,6-dimethyl-3-amino phenol, 3-ureido phenol, 3-chloro-6-acetylaminophenol, 2-methyl-5-methylamino phenol, 2-acetylamino phenol, m-amino phenol, 2,6-dimethyl-3-ureido phenol, 3-methoxy phenol, 3-acetylamino phenol, 2-methyl-5-carbamylmethylamino phenol, 2-methyl-5-N-(β-hydroxyethylamino) phenol, 2,3-xylenol, 2-methyl-5-carbethoxyamino phenol and 2,6-xylenol.

Representative paraphenylene diamines usefully employed in the present invention include the following: 2-methyl-4-N-(ethyl, carbamylmethyl) amino aniline, 2-methyl-4-N-(ethyl, β-mesylaminoethyl) amino aniline, 2-methyl-4-N-ethyl, β-sulfoethyl) amino aniline, 4-N-(ethyl, β-piperidinoethyl) amino aniline, 4-N-(ethyl, carbamylmethyl) amino aniline, 4-N-(ethyl, β-mesylaminoethyl) amino aniline, N,N-di-β-hydroxyethyl paraphenylenediamine, N-[(4-amino) phenyl] morpholine, N-[(4-amino) phenyl] piperidine, 4-amino-N,N-(ethyl, benzoylaminoethyl) aniline, and 3-methyl-4-N,N-(ethyl, β-mesylaminoethyl) amino aniline.

The proportion of paraphenylenediamine to phenol can range between 3:1 and 1:1 and preferably between 1.2:1 and 1:1.

In a second embodiment of the present invention when Z represents NO, the phenolic compound of formula III is condensed on a nitroso derivative of paraphenylene diamine of the formula V

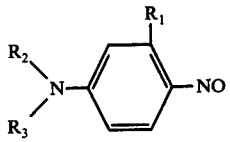

wherein $R_1$ and $R_6$ have the meanings given above. This condensation is carried out in an aqueous or hydroalcoholic medium, preferably hydroethanolic, at a temperature between about 30° to 60° C and preferably between 40° and 55° C.

Representative nitroso derivatives usefully employed can include the following: 4-nitroso-N-(ethyl, β-piperidinoethyl) aniline, 4-nitroso-N-(ethyl, β-morpholinoethyl) aniline, 4-nitroso-N-(ethyl, β-sulfoethyl) aniline, 4-nitroso-N-(di-β-hydroxyethyl) aniline, 3-methyl-4-nitroso-N-(ethyl, β-acetylaminoethyl) aniline, 3-methoxy-4-nitroso-N-(di-β-hydroxyethyl) aniline, 3-chloro-4-nitroso-N-(di-β-hydroxyethyl) aniline, 3-methyl-4-nitroso-N,N-(ethyl, β-benzoylaminoethyl) aniline, 3-methyl-4-nitroso-N,N-(di-β-hydroxyethyl) aniline, 4-nitroso-N,N-(ethyl, β-mesylaminoethyl) aniline.

The proportion of the nitroso derivative to the phenolic compound generally ranges between about 2:1 and 1:1 and preferably between about 1.2:1 and 1:1.

The compounds in which $R_1$ is in position ortho with respect to the group —$NR_2R_3$ and $R_5$ is amino can be obtained by hydrolysis of the corresponding 3-acetylated derivative with a base such as sodium hydroxide.

The present invention also relates to dyes obtained by the condensation of a compound of formula II on a compound of formula III, as well as amino dyes obtained by the hydrolysis of compounds acetylated in the 3 position.

These dyes can be used to dye keratinic fibers and in particular living human hair.

Indoanilines, in particular those described in Luxembourg Pats. No. 58,848 of assignee, which carry a primary amine group are of course known.

The indoanilines according to the present application are considered to be an improvement over known indoanilines. In particular $R_2$ and $R_3$ permit a variation of the dye properties according to needs wherein the solubility of the dye is improved or diminished and wherein the affinity of the dye for the fibers can be improved as well as its resistance to washing and to light.

Moreover, the indoanilines according to the present invention permit an enlargement of the range of colors obtainable thus for example, shades of green and shades of orange-beige never attained up to the present can be achieved using the indoanilines of the present invention.

The present invention also has for an object a dye composition for keratinic fibers, in particular for living human hair, characterized by the fact that they include in an aqueous or hydroalcoholic solution at least one compound of formula I.

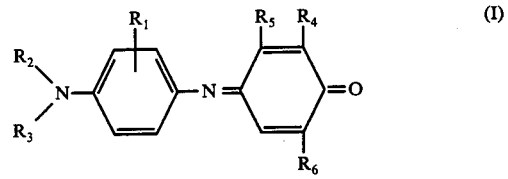

wherein
$R_1$ represents hydrogen, halogen, alkyl or alkoxy;
$R_2$ represents alkyl, hydroxyalkyl, carbamylalkyl, piperidinoalkyl, morpholinoalkyl, sulfoalkyl, dialkylaminoalkyl, acylaminoalkyl (preferably acetylaminoalkyl or benzoylaminoalkyl) and mesylaminoalkyl;
$R_3$ represents hydroxyalkyl, carbamylalkyl, piperidinoalkyl, morpholinoalkyl, sulfoalkyl, dialkylaminoalkyl, acylaminoalkyl, (preferably acetylaminoalkyl or benzoylaminoalkyl), mesylaminoalkyl; or $R_2$ and $R_3$ together with a nitrogen atom to which they are attached form a heterocycle selected from piperidino or morpholino; and
$R_4$, $R_5$ and $R_6$ each independently represent hydrogen, halogen, alkyl, alkoxy, acylamino, ureido or carbalkoxyamino and $R_5$ can also represent amino, alkylamino, hydroxyalkylamino or carbamylalkylamino, the alkyl and alkoxy groups being able to contain from 1 to 6 carbom atoms and the acyl group containing 2 to 7 carbon atoms. It is understood that the above compounds can be present in tautomeric forms of that represented by formula I.

These dye compositions generally include from 0.02% to 2% and preferably from 0.05% to 1% of the compound of formula I based on the total weight of the composition.

The dye compositions according to the present invention can include only the indoanilines of formula I.

It is however possible to mix the dyes according to the present invention with other dyes conventionally utilized for the dyeing of hair, for example, nitrobenzene dyes, azo dyes, anthraquinones, indamines, indophenols and/or other indoanilines.

The compositions according to the present invention generally are provided in the form of an aqueous or hydroalcoholic solution containing one or more compounds of formula I in mixture or not with other dyes. They can however also include thickening agents and be present in the form of creams or gels.

Representative thickening agents usefully employed in the dye compositions of the present invention include for instance, cellulosic derivatives such as methylcellulose, hydroxyethylcellulose, carboxymethylcellulose or acrylic polymers such as sodium salt of polyacrylic acid or carboxyvinyl polymers.

The dye composition of the present invention can include as solvents water, lower alkanols, for example ethanol or isopropanol, polyalcohols such as glycols, for example ethylene glycol, propyleneglycol, butylglycol, diethyleneglycol, and the monomethyl ether of diethyleneglycol.

The compositions according to the present invention can also include various components conventionally employed in cosmetic compositions such as wetting agents for example oxyethylenated alkylphenols, oxyethylenated fatty acids, oxyethylenated fatty alcohols, sulfates and sulfonates of fatty alcohols, optionally oxyethylenated, dispersing agents, swelling agents, penetrating agents, emollients, polymers and/or perfumes. They can also be packaged in aerosol containers in the presence of a gaseous propellant.

Representative gaseous propellants include nitrogen, nitrous oxide, volatile hydrocarbons such as butane, isobutane or propane, or preferably the fluoronated hydrocarbons such as those sold under the name of Freon including dichlorodifluoromethane, 1,1-difluoromethane, 1,2-dichloro-1,1,2,2-tetrafluoromethane or 1-chloro-1,1-difluoromethane. Mixtures of two or more of the above hydrocarbons or fluoronated hydrocarbons can also be employed.

The pH of the compositions can vary within wide limits. The pH generally ranges between 4 and 11, preferably between 6.5 and 10.5 and advantageously between 7 to 9.

The pH of the composition can be adjusted by the use of an alkalizing agent for example, ammonia, mono-, di- or triethanolamine, di- or trisodium phosphate, sodium or potassium carbonate or with the use of acidifying agent, such as for example, acedic acid, lactic acid, phosphoric acid and citric acid.

The dyeing of keratinic fibers, in particular living human hair, using the dye compositions of the present invention can be carried out in a conventional manner by applying the composition to the fibers to be dyed, leaving the same in contact therewith for a period ranging between 5 to 30 minutes, followed by rinsing and eventually washing and drying the fibers.

The compositions according to the present invention, when they are present in the form of a hydroalcoholic solution, can also include a cosmetic film-forming resin, in which case the composition comprise a colored hair-setting lotion which can be applied to the wet hair prior to setting the same.

Representative cosmetic film-forming resins usefully employed in the composition of the present invention include for instance film-forming polymers such as: polyvinylpyrrolidone, copolymers of vinylpyrrolidone and vinyl acetate, copolymers of vinyl acetate and an unsaturated carboxylic acid such as crotonic acid, copolymers resulting from the copolymerization of vinyl acetate, crotonic acid and an acrylic or methacrylic ester, copolymers resulting from the copolymerization of vinylacetate and an alkylvinyl ether, copolymers resulting from the copolymerization of vinyl acetate, crotonic acid and a vinyl ester of a long carbon chain acid or even an allyl or methallyl ester of a long carbon chain acid, copolymers resulting from the copolymerization of an ester derived from an unsaturated alcohol and a short carbon chain acid, an unsaturated short carbon chain acid and at least one ester derived from an unsaturated short chain alcohol and an unsaturated acid, copolymers resulting from the copolymerization of at least an unsaturated ester and at least an unsaturated acid.

Representative resins include polyvinylpyrrolidone having a molecular weight of 10,000 to 360,000, copolymers of 10% crotonic acid and 90% vinyl acetate having a molecular weight of 10,000 to 70,000, copolymers of vinylpyrrolidone (PVP) and vinyl acetate (VA) having a molecular weight of 30,000 to 200,000, the ratio of PVP to VA being between about 30:70 and 70:30, copolymers of maleic anhydride and methylvinyl ether in a molar ratio of 1:1 and having specific viscosity measured at 25° C at a concentration of 1 g in 100 cc of methylethylketone between about 0.1 and 3.5, the monoethylester, monoisopropylester and monobutylester of maleic anhydride methylvinyl ether copolymers, the copolymer of maleic anhydride and butylvinylether in a molar ratio of 1:1, the terpolymers of methyl methacrylate (15–25%)-stearyl methacrylate (18–28%)-dimethyl methacrylate (52–62%), and the terpolymers of vinyl acetate (75–85%)-allyl stearate (10–20%)-allyloxyacetic acid (3–10%).

These resins are generally used in amounts between about 1 and 3% based on the total weight of the composition.

The alcohols generally used in the hair setting lotion compositions of the present invention are low molecular weight alcohols and preferably are ethanol or isopropanol. These alcohols are generally employed in amounts of 20 to 70% by weight of the total composition.

The hair setting lotion compositions of the present invention are employed in the conventional manner by applying the same to wet or damp hair previously washed and rinsed, followed by rolling the same on rollers and drying the hair.

The following examples illustrate the present invention. Unless otherwise indicated, all parts and percentages are by weight.

EXAMPLE 1

Preparation of N-[(4'-ethyl, carbamylmethyl amino-2'-methyl)phenyl]-2,6-dimethyl-3-amino benzoquinoneimine

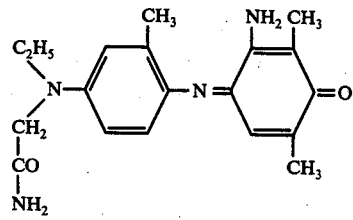

0.025 mole (3.4 g) of 2,6-dimethyl-3-amino phenol and 0.025 mole (5.2 g) of 2-methyl-4-N-(ethyl, carbamylmethyl) amino aniline are dissolved in 100 cc of isopropyl alcohol, 100 cc of water and 60 cc of ammonia at 22° Bé. To the resulting solution there are then added 100 g of crushed ice and then little by little, with good agitation, 0.05 mole (11.4 g) of ammonium persulfate in 50 cc of water. At the end of this addition, the above indoaniline which has precipitated is filtered and the raw product is washed with water, recrystallized in a mixture of dimethylformamide and water and dried under a vacuum. It exhibits a melting point of 220° C.

| Analysis | Calculated For $C_{19}H_{24}N_4O_2$ | Found | |
|---|---|---|---|
| C% | 67.03 | 67.20 | 67.09 |
| H% | 7.11 | 6.92 | 6.81 |
| N% | 16.46 | 16.28 | 16.37 |

EXAMPLE 2

Preparation of N-[(4'-ethyl,β-piperidinoethyl amino)-phenyl]-2,6-dimethyl-3-acetylamino benzoquinoneimine

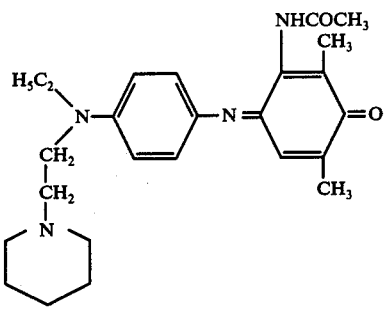

0.01 mole (1.79 g) of 2,6-dimethyl-3-acetylamino phenol is dissolved in 15 cc of acetone to which have been added 15 cc of ammonia at 22° Bé. To this resulting solution, cooled to 0° C, there are added simultaneously with the use of a double funnel, little by little and with agitation, 0.01 mole (3.56 g) of the trihydrochloride of 4-N-(ethyl, β-piperidinoethyl) amino aniline in 20 cc of water and 0.02 mole (4.56 g) of ammonium persulfate in 20 cc of water. At the end of this addition, the above indoaniline which has precipitated is filtered therefrom. After washing with water, recrystallizing in a hydroacetonic mixture and drying under a vacuum, the above product exhibits a melting point of 94° C.

| Analysis | Calculated For $C_{25}H_{34}N_4O_2$ | Found | |
|---|---|---|---|
| C% | 71.06 | 71.15 | 71.12 |
| H% | 8.11 | 8.05 | 8.27 |
| N% | 13.26 | 13.34 | 13.12 |

EXAMPLE 3

Preparation of N-[(4'-ethyl, carbamylmethyl amino) phenyl]-2,6-dimethyl-3-amino benzoquinoneimine

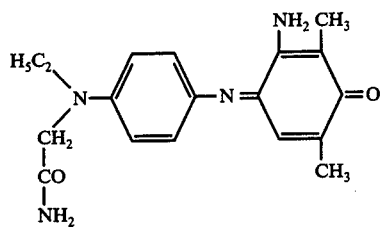

0.4 mole (69.5 g) of the hydrochloride of 2,6-dimethyl-3-amino phenol and 0.4 mole (77.3 g) of 4-N-(ethy, carbamylmethyl) amino aniline are dissolved in 800 cc of isopropanol, 1500 cc of water and 960 cc of ammonia at 22° Bé. There are then added 1200 g of crushed ice and little by little, while maintaining the temperature of the reaction mixture near 0° C, 0.44 mole (100 g) of ammonium persulfate in 800 cc of water. The agitation of the reaction mixture is continued for an additional hour at which time the above indoaniline is filtered and after washing it with water and recrystallizing the same in a mixture of dimethylformamide and water, it exhibits a melting point of 218° C.

| Analysis | Calculated For $C_{18}H_{22}N_4O_2$ | Found | |
|---|---|---|---|
| C% | 66.23 | 66.38 | 66.17 |
| H% | 6.79 | 6.77 | 6.79 |
| N% | 17.17 | 17.06 | 17.12 |

EXAMPLE 4

Preparation of N-[(4'-ethyl, β-mesylaminoethyl amino-2'-methyl) phenyl]-2-methyl-5-amino benzoquinoneimine.

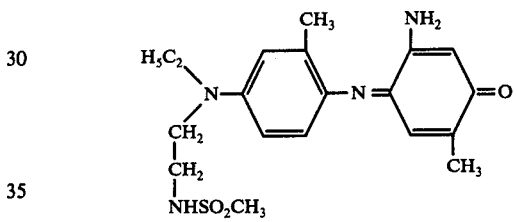

0.12 mole (14.8 g) of 2-methyl-5-amino phenyl and 0.12 mole (32.5 g) of 2-methyl-4-N-(ethyl, β-mesylaminoethyl) amino aniline are dissolved in 450 cc of water to which have been added 450 cc of acetone and 300 cc of ammonia at 22° Bé. There are then added 350 g of crushed ice and, little by little with good agitation, and while maintaining the temperature of the reaction mixture at about 0° C, there is added 0.24 mole (54.8 g) of ammonium persulfate in 180 cc of water. At the end of the addtion of these materials the reaction mixture is continued to be agitated for an additional 30 minutes. The above indoaniline which precipitates first in the form of an oil, slowly crystallizes and is then filtered, washed with water and recrystallized in a mixture of demethylformamide and water. After drying under a vacuum the product exhibits a melting point of 145° C.

| Analysis | Calculated For $C_{19}H_{26}N_4O_3S$ | Found | |
|---|---|---|---|
| C% | 58.45 | 58.30 | 58.27 |
| H% | 6.71 | 6.84 | 6.99 |
| N% | 14.35 | 14.19 | 14.21 |
| S% | 8.19 | 8.28 | 8.28 |

EXAMPLE 5

Preparation of N-[(4'-ethyl, carbamylmethyl amino-2'-methyl) phenyl]-2-methyl-5-ureido benzoquinoneimine.

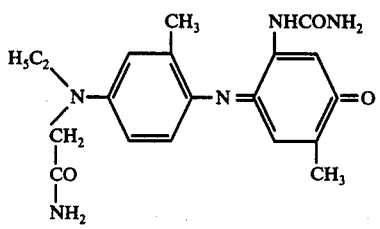

Initially, 0.02 mole (3.32 g) of 2-methyl-5-ureido phenol is dissolved in 100 cc of isopropyl alcohol and 100 cc of ammonia at 22° Bé. There is also dissolved 0.022 mole (4.6 g) of 2-methyl-4'-N-(ethyl, carbamylmethyl) amino aniline in 20 cc of water to which have been added 5 cc of hydrochloric acid ($d=1.18$). The resulting two solutions are then mixed together and to the resulting mixture there are added 160 g of ice, and then little by little with agitation, while maintaining the temperature of the reaction mixture near 0° C, 0.044 mole (10.1 g) of ammonium persulfate in 30cc of water is introduced therein. The above raw indoaniline which precipitates is then filtered, washed with water and recrystallized in a mixture of dimethylformamide and water. After drying under a vacuum the product exhibits a melting point of 198° C.

| Analysis | Calculated For $C_{19}H_{23}O_3N_5$ | Found | |
|---|---|---|---|
| C% | 61.79 | 61.50 | 61.65 |
| H% | 6.23 | 6.12 | 6.19 |
| N% | 18.97 | 18.86 | 18.77 |

EXAMPLE 6

Preparation of N-[(4'-ethyl, carbamylmethyl amino-2'-methyl)phenyl]-2-methyl-5-acetylamino benzoquinoneimine.

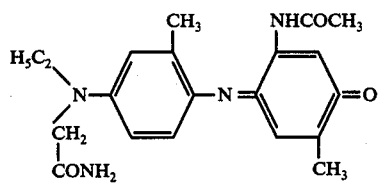

0.02 mole (3.3 g) of 2-methyl-5-acetylamino phenol is dissolved in 100 cc of isopropyl alcohol, 150 cc of water and 100 cc of ammonia at 22° Bé. There is also dissolved 0.022 mole (4.6 g) of 2-methyl-4-N-(ethyl, carbamylmethyl) amino aniline in 20 cc of water to which have been added 5 cc of hydrochloric acid ($d = 1.18$). The resulting two solutions are combined and there is added thereto, little by little with agitation, while maintaining the resulting reaction mixture at a temperature near 0° C, 0.044 mole (10.1 g) of ammonium persulfate in 30 cc of water. The raw indoaniline which has precipitated is then filtered and after washing it with water and then with acetone and recrystallizing the same in a mixture of dimethylformamide and water, the product is dried under a vacuum. It exhibits a melting point of 205° C.)

| Analysis | Calculated For $C_{20}H_{24}N_4O_3$ | Found | |
|---|---|---|---|
| C% | 65.21 | 65.23 | 65.05 |
| H% | 6.52 | 6.52 | 6.58 |
| N% | 15.21 | 15.14 | 14.98 |

EXAMPLE 7

Preparation of N-[(4'-ethyl,β-mesylaminoethyl amino-2'-methyl)phenyl]-2,6-dimethyl-3-acetylamino benzoquinoneimine.

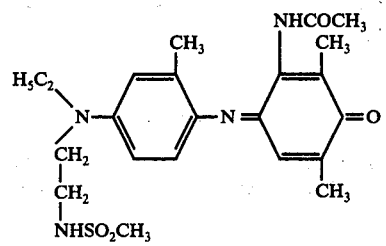

0.07 mole (12.55 g) of 2,6-dimethyl-3-acetylamino phenol and 0.07 mole (19 g) of 2-methyl-4-N-(ethyl,β-mesylaminoethyl) amino aniline are dissolved in 260 cc of water to which have been added 260 cc of acetone and 175 cc of ammonia at 22° Bé. There are then added 200 g of crushed ice to the resulting mixture and then little by little with good agitation, while maintaining the temperature of the reaction mixture near 0° C, there is added 0.14 mole (32 g) of ammonium persulfate in 200 cc of water. At the end of this addition the agitation of the reaction mixture is continued for an additional 30 minutes. The above indoaniline which has precipitated is then filtered, washed with water, recrystallized in a mixture of dimethylformamide and water and dried under a vacuum. It exhibits a melting point of 171° C.

| Analysis | Calculated For $C_{22}H_{30}N_4O_4S$ | Found | |
|---|---|---|---|
| C% | 59.18 | 59.03 | 58.85 |
| H% | 6.77 | 6.79 | 6.85 |
| N% | 12.55 | 12.23 | 12.29 |
| S% | 7.16 | 7.27 | 7.21 |

EXAMPLE 8

Preparation of N-[(4'-(ethyl, β-mesylaminoethyl-)amino-2'-methyl) phenyl]-2,6-dimethyl-3-amino benzoquinoneimine.

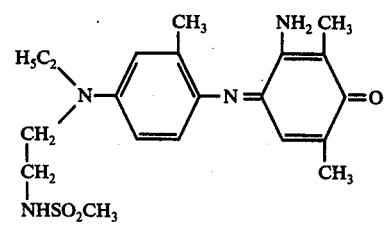

0.15 mole (20.5 g) of 2,6-dimethyl-3-amino phenol and 0.15 mole (40.65 g) of 2-methyl-4-N-(ethyl,β-mesylaminoethyl) amino aniline are dissolved in 560 cc of water to which have been added 560 cc of acetone and 375 cc of ammonia at 22° Bé. There are then added 450 g of crushed ice and little by little while maintaining the temperature of the reaction mixture near 0° C, there is added 0.30 mole (68.4 g) of ammonium persulfate in 220 cc of water. At the end of this addition the agitation of the reaction mixture is continued for 30 minutes. The above indoaniline which has precipitated is then filtered, washed with water, recrystallized in a mixture of dimethylformamide and water and dried under a vacuum at 80° C. The above product exhibits a melting point of 166° C.

| Analysis | Calculated For $C_{20}H_{28}N_4O_3S$ | Found | |
|---|---|---|---|
| C% | 59.39 | 59.35 | 59.34 |
| H% | 6.98 | 7.19 | 6.94 |
| N% | 13.85 | 13.68 | 13.84 |
| S% | 7.91 | 8.04 | 8.00 |

EXAMPLE 9

Preparation of N-[(4'-di-β-hydroxyethylamino) phenyl]-2,6-dimethyl-3-amino benzoquinoneimine.

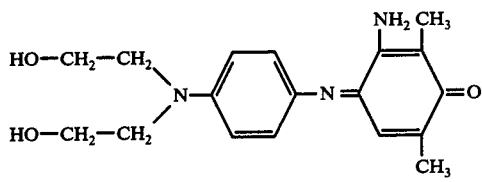

0.01 mole (1.73 g) of 2,6-dimethyl-3-amino phenol and 0.011 mole (2.1 g) of N,N-di-β-hydroxyethyl paraphenylenediamine are dissolved in 40 cc of water to which have been added 10 cc of ammonia at 22° Bé. While maintaining the temperature of the reaction mixture at 0° C, there is then added little by little, with agitation, 0.022 mole (5 g) of ammonium persulfate in 25 cc of water. The above indoaniline which has precipitated is then filtered, washed with water, recrystallized in a mixture of dimethylformamide and water and dried under a vacuum. It exhibits a melting point of 190° C.

| Analysis | Calculated For $C_{18}H_{23}N_3O_3$ | Found | |
|---|---|---|---|
| C% | 65.63 | 65.42 | 65.39 |
| H% | 7.04 | 7.15 | 7.02 |
| N% | 12.76 | 12.92 | 12.92 |

EXAMPLE 10

Preparation of N-[(4'-ethyl,carbamylmethyl amino-2'-methyl) phenyl]-2-methyl-5-amino benzoquinoneimine.

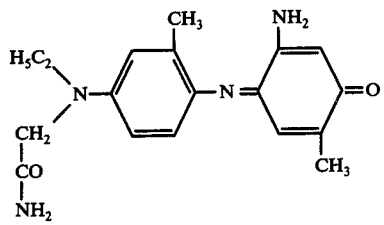

0.005 mole (0.62 g) of 2-methyl-5-amino phenol and 0.005 mole of 2-methyl-4-N-(ethyl, carbamylmethyl) amino aniline (1.03g) are dissolved in 25 cc of water to which have been added 10 cc of acetone and 20 cc of a normal sodium hydroxide solution. To the resulting solution, cooled in ice, there is then added little by little with agitation 0.01 mole (2.3 g) of ammonium persulfate in 23 cc of water. The above indoaniline which has precipitated is then filtered, washed with water, recrystallized in a mixture of dimethylformamide and water and dried under a vacuum. It exhibits a melting point of 225° C.

| Analysis | Calculated For $C_{18}H_{22}N_4O_2$ | Found | |
|---|---|---|---|
| C% | 66.25 | 66.12 | 66.17 |
| H% | 6.75 | 6.85 | 6.90 |
| N% | 17.17 | 17.07 | 17.11 |

EXAMPLE 11

Preparation of N-[(4'-ethyl,β-mesylaminoethyl amino-2'-methyl) phenyl]-2,5-dimethyl benzoquinoneimine.

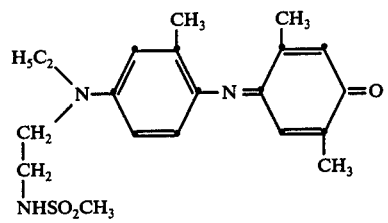

0.005 mole (0.61 g) of 2,5-xylenol and 0.005 mole (1.36 g) of 2-methyl-4-N-(ethyl,β-mesylaminoethyl) amino aniline are dissolved in 50 cc of a 0.5 N sodium hydroxide solution to which have been added 20 cc of ethanol. To the resulting solution, cooled in ice, there is then added, little by little, with agitation, 0.01 mole (2.3 g) of ammonium persulfate in 23 cc of water. The indoaniline, which first precipitates in the form of an oil, crystallizes slowly. The indoaniline is then filtered, washed with water and recrystallized in isopropanol. It melts at 118° C.

| Analysis | Calculated For $C_{20}H_{27}N_3O_3S$ | Found | |
|---|---|---|---|
| C% | 61.72 | 61.52 | 61.53 |
| H% | 6.94 | 7.02 | 6.96 |
| N% | 10.79 | 10.65 | 10.75 |
| S% | 8.22 | 8.45 | 8.33 |

EXAMPLE 12

Preparation of N-[(4'-ethyl, β-acetylaminoethyl amino-2'-methyl) phenyl]-2,6-dimethyl-3-amino benzoquinoneimine.

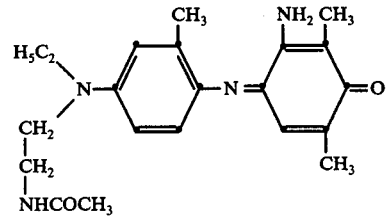

0.01 mole (1.38 g) of 2,6-dimethyl-3-amino phenol and 0.01 mole (2.85 g) of the hydrochloride of 3-methyl-4-nitroso-N-(ethyl, β-acetylaminoethyl) aniline are dissolved in 50 cc of a 50% hydroethanolic solution. The resulting solution is heated for one hour at 40° C. After cooling and adding thereto 20 cc of water, the above indoaniline precipitates and is filtered therefrom. The filtered indoaniline is then washed with water and recrystallized in a mixture of dimethylformamide and water and after drying under a vacuum, exhibits a melting point of 196° C.

| Analysis | Calculated for $C_{21}H_{28}N_4O_2$ | Found | |
|---|---|---|---|
| C% | 68.45 | 68.16 | 68.23 |
| H% | 7.66 | 7.50 | 7.72 |
| N% | 15.21 | 15.41 | 15.10 |

EXAMPLE 13

Preparation of N-[(4'-ethyl,β-mesylaminoethyl amino-2'-methyl) phenyl]-2-methyl-5-acetylamino benzoquinoneimine.

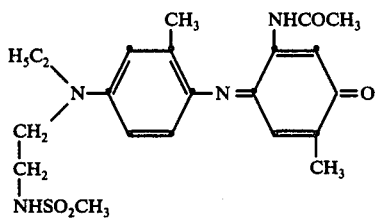

0.02 mole (3.3 g) of 2-methyl-5-acetylamino phenol and 0.02 mole (5.42 g) of 2-methyl-4-N-(ethyl-β-mesylaminoethyl) amino aniline are dissolved in 150 cc of a 50% hydroisopropanolic solution to which have been added 50 cc of ammonia at 22° Bé. There are then added 60 g of crushed ice and little by little with agitation, there is introduced 0.022 mole (5.02 g) of ammonium persulfate in 25 cc of water while maintaining the temperature of the reaction mixture at about 0° C. At the end of this addition, the above indoaniline which precipitates is then filtered, washed with water, recrystallized in a mixture of dimethylformamide and water and dried under a vacuum. The product exhibits a melting point of 185° C.

| Analysis | Calculated for $C_{21}H_{28}N_4O_4S$ | Found | |
|---|---|---|---|
| C% | 58.33 | 58.17 | 58.09 |
| H% | 6.48 | 6.40 | 6.52 |
| N% | 12.96 | 12.69 | 12.94 |

EXAMPLE 14

Preparation of N-[4'-di-β-hydroxyethylamino) phenyl]-2-ureido benzoquinoneimine.

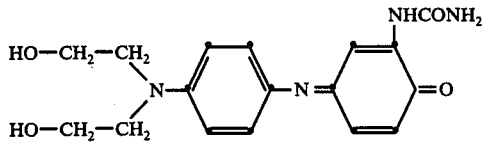

0.01 mole (1.52 g) of 2-ureido-phenol and 0.01 mole (1.96 g) of N,N-di-β-hydroxyethyl paraphenylenediamine are dissolved in 50 cc of water to which have been added 10 cc of ammonia of 22° Bé. To the resulting solution, cooled in ice, there is then added, little by little, with agitation, 0.01 mole (3.29 g) of potassium ferricyanide in 25 cc of water. At the end of this addition, the above indoaniline which has precipitated is filtered, washed with water, and dried under a vacuum. The product is chromatographically pure and melts at a temperature of 139° C.

| Analysis | Calculated For $C_{17}H_{20}N_4O_4$ | Found | |
|---|---|---|---|
| C% | 59.29 | 59.38 | 59.16 |
| H% | 5.85 | 5.90 | 6.12 |
| N% | 16.27 | 16.38 | 16.14 |

EXAMPLE 15

Preparation of N-[(4'-di-β-hydroxyethyl amino) phenyl]-2,6-dimethyl-3-acetylamino benzoquinoneimine, monohydrate.

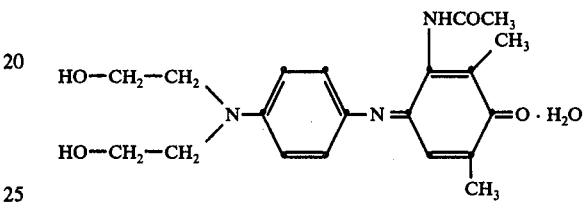

0.1mole (17.9 g) of 2,6-dimethyl-3-acetylamino phenol and 0.1 mole (19.6 g) of N,N-di-β-hydroxyethyl paraphenylenediamine are dissolved in 500 cc of a 50% hydroisopropanolic solution to which have been added 100 cc of ammonia at 22° Bé. To the resulting mixture there are added 300 g of crushed ice, and then little by little with agitation, 0.2 mole (45.6 g) of ammonium persulfate in 150 cc of water. At the end of the addition the agitation of the reaction mixture is continued for an additional 15 minutes. The above-identified indoaniline is then filtered; washed first with water and then with acetone, recrystallized in a mixture of dimethylformamide and water and dried under a vacuum. The product exhibits a melting point of 92° C.

| Analysis | Calculated for $C_{20}H_{25}O_4N_3 \cdot H_2O$ | Found | |
|---|---|---|---|
| C% | 61.60 | 61.42 | 61.42 |
| H% | 6.94 | 6.67 | 6.81 |
| N% | 10.79 | 10.64 | 10.99 |

EXAMPLE 16

Preparation of N-[(4'-di-β-hydroxyethyl amino) phenyl]-2-methyl-5-acetylamino benzoquinoneimine.

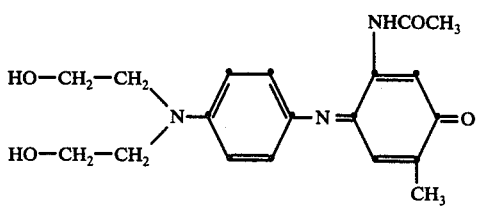

0.1 mole (16.5 g) of 2-methyl-5-acetylamino phenol and 0.1 mole (19.6 g) of N,N-di-β-hydroxy-ethyl paraphenylenediamine are dissolved in 500 cc of a 50% hydroisopropanolic solution to which have been added in 500 cc of a 50% hydroisopropanolic solution to which have been added 100 cc of ammonia at 22° Bé. To the resulting mixture there are added 300 g of crushed ice and then little by little and with good agitation 0.2 mole (45.6 g) of ammonium per sulfate in 150 cc of water. At the end of the addition, the agitation of the reaction mixture is continued for 15 minutes. The above indoaniline is then filtered, washed with water and then with acetone, recrystallized in a mixture of dimethylformamide and water and dried under vacuum. The product exhibits a melting point of 198° C.

| Analysis | Calculated for $C_{19}H_{23}O_4N_3$ | Found | |
|---|---|---|---|
| C% | 63.86 | 63.75 | 64.02 |
| H% | 6.44 | 6.48 | 6.42 |
| N% | 11.76 | 11.63 | 11.82 |

EXAMPLE 17

Preparation of N-[(4'-ethyl,β-piperidinoethyl amino) phenyl]-2,6-dimethyl-3-amino benzoquinoneimine, monohydrochloride, monohydrate.

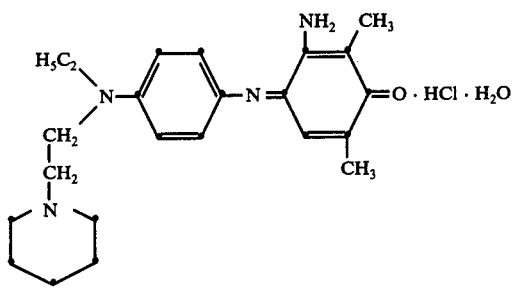

0.01 mole (3.34 g) of the dihydrochloride of 4-nitroso-N-ethyl-N-β-piperidinoethyl aniline and 0.01 mole (1.73 g) of the hydrochloride of 2,6-dimethyl-3-amino phenol are dissolved in 40 cc of a 0.5 N sodium hydroxide solution. The resulting reaction mixture is permitted to stand overnight at ambient temperature. Thereafter, the above indoaniline which precipitates under the form of the monohydrate, monohydrochloride crystals is the filtered, washed first with water and then with acetone and dried under a vacuum. The product melts with the decomposition at 194° C.

| Analysis | Calculated for $C_{23}H_{35}N_4ClO_2$ | Found | |
|---|---|---|---|
| C% | 63.70 | 63.53 | 63.80 |
| H% | 8.06 | 7.89 | 7.90 |
| N% | 12.90 | 12.58 | 12.61 |
| Cl% | 8.20 | 8.25 | 8.34 |

EXAMPLE 18

Preparation of N-[(4'-ethyl,β-benzoylamino ethyl amino-2'-methyl)phenyl]-2,6-dimethyl-3-amino benzoquinoneimine.

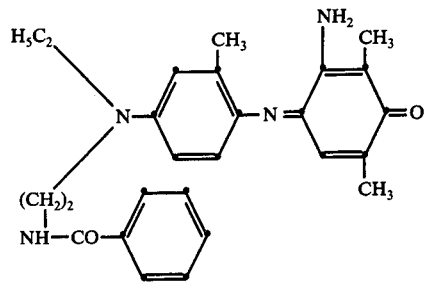

0.01 mole (3.48 g) of the hydrochloride of 3-methyl-4-nitroso-N-ethyl-N-β-benzoylaminoethyl aniline and 0.01 mole (1.73 g) of the hydrochloride of 2,6-dimethyl-3-amino phenol are dissolved in 40 cc of a 0.5 N sodium hydroxide solution to which have been added 30 cc of ethanol. The resulting reaction mixture is stirred for 2 hours at 40° C, cooled and then alkalinized with the aid of ammonia at 22° Bé. The above indoaniline which precipitates is then filtered, washed with water and recrystallized in acetone. After drying under a vacuum, the product exhibits a melting point of 222° C.

| Analysis | Calculated for $C_{26}H_{30}N_4O_2$ | Found | |
|---|---|---|---|
| C% | 72.53 | 72.47 | 72.42 |
| H% | 7.02 | 7.18 | 7.17 |
| N% | 13.01 | 13.09 | 12.91 |

EXAMPLE 19

Preparation of N-[(4'-ethyl, carbamylmethyl amino-2'-methyl) phenyl]-2-chloro-5-amino benzoquinoneimine.

0.01 mole (2.07 g) of 2-methyl-4-N-(ethyl, carbamylmethyl) amino aniline and 0.01 mole (1.43 g) of 2-chloro-5-amino phenol are dissolved with agitation in 40 cc of water to which have been added 10 cc of isopropanol and 10 cc of ammonia at 22° Bé. There is then added, little by little with agitation, to this mixture, cooled to 0° C, 0.01 mole (3.29 g) of potassium ferricyanide in solution in 25 cc of water. At the end of this addition, the above indoaniline which precipitates is filtered, washed with water, and recrystallized in a mixture of dimethylformamide and water. It is then recrystallized in hydroacetonic mixture and dried under a vacuum. The resulting product exhibits a melting point of 220° C.

| Analysis | Calculated for $C_{17}H_{19}N_4ClO_2$ | Found | |
|---|---|---|---|
| C% | 58.87 | 58.94 | 59.04 |
| H% | 5.53 | 5.66 | 5.70 |
| N% | 16.16 | 16.25 | 16.32 |

EXAMPLE 20

Preparation of N-[(4'-ethyl, β-morpholinoethyl amino) phenyl[-2-methyl-5-amino benzoquinoneimine.

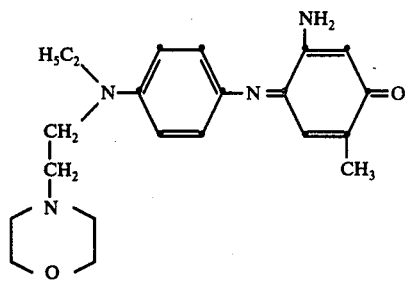

0.01 mole (3.36 g) of the dihydrochloride of 4-nitroso-N-(ethyl, β-morpholinoethyl) aniline and 0.01 mole (1.23 g) of 2-methyl-5-amino-phenol are dissolved in 40 cc of the 0.5 N sodium hydroxide solution to which have been added 10 cc of ethanol. The resulting reaction mixture is stirred for two hours at 40° C. After cooling there are added thereto 10 cc of a 1N sodium hydroxide solution. The above indoaniline which precipitates is then filtered, washed with water, recrystallized in a hydroacetonic mixture and dried under a vacuum. The resulting product melts at 93° C.

| Analysis | Calculated for $C_{21}H_{28}N_4O_2$ | Found | |
|---|---|---|---|
| C% | 68.45 | 68.27 | 68.34 |
| H% | 7.66 | 7.68 | 7.68 |
| N% | 15.21 | 15.39 | 15.26 |

EXAMPLE 21

Preparation of N-[(4'-di-β-hydroxyethyl amino) phenyl]-2-chloro-5-amino benzoquinoneimine.

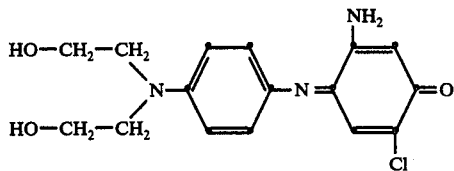

0.01 mole (2.46 g) of the hydrochloride of 4-nitroso-di-β-hydroxyethylaniline and 0.01 mole of 2-chloro-5-amino phenol are introduced into 20 cc of a 0.5 N sodium hydroxide solution to which have been added 5 cc of ethanol. The resulting reaction mixture is maintained under agitation for 3 hours at 55° C. After cooling, the above indoaniline which precipitates, is then filtered, washed with water, recrystallized in a mixture of dimethylformamide and water and dried under a vacuum. It exhibits a melting point of 213° C.

| Analysis | Calculated for $C_{16}H_{18}N_3Cl\,O_3$ | Found | |
|---|---|---|---|
| C% | 57.22 | 57.14 | 57.20 |
| H% | 5.35 | 5.22 | 5.27 |
| N% | 12.51 | 12.47 | 12.54 |
| Cl% | 10.58 | 10.56 | 10.56 |

EXAMPLE 22

Preparation of N-[(4'-di-β-hydroxyethyl amino) phenyl]-2-chloro-5-acetylamino benzoquinoneimine.

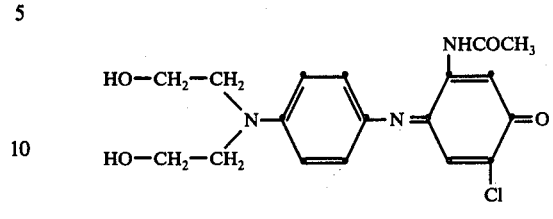

0.01 mole (1.96 g) of N,N-di-β-hydroxy-ethyl para-phenylenediamine and 0.01 mole (1.85 g) of 2-chloro-5-acetylamino phenol are dissolved in 40 cc of a 1.25 N sodium hydroxide solution. To the resulting solution, cooled to 0° C, there is added little by little with agitation, 0.02 mole (4.6 g) of ammonium persulfate in 20 cc of water. At the end of this addition, the reaction mixture is continued to be agitated for 15 minutes. The above indoaniline which precipitates is then filtered, washed first with water and then with acetone, and dried under a vacuum. The product exhibits a melting point of 210° C.

| Analysis | Calculated for $C_{18}H_{20}O_4N_3Cl$ | Found | |
|---|---|---|---|
| C% | 57.22 | 57.13 | 57.00 |
| H% | 5.30 | 5.37 | 5.41 |
| N% | 11.12 | 11.10 | 11.05 |

EXAMPLE 23

Preparation of N-[(4'-di-β-hydroxyethyl amino) phenyl]-3-chloro-6-acetylamino benzoquinoneimine.

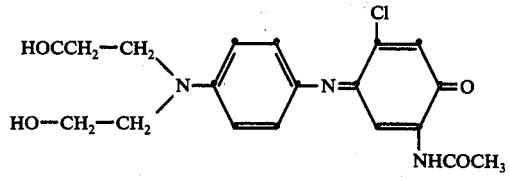

0.01 mole (1.96 g) of N,N-di-β-hydroxyethyl para-phenylenediamine and 0.01 mole (1.85 g) of 3-chloro-6-acetylamino phenol are dissolved in 50 cc of a 1 N sodium hydroxide solution. To the resulting solution, cooled to 0° C, there is added, little by little, with agitation, 0.02 mole (4.6 g) of ammonium persulfate in 20 cc of water. At the end of this addition, the above indoaniline which precipitates is filtered, washed with water and then recrystallized first in a hydroacetonic mixture and then in a mixture of dimethylformamide and water. After drying under a vacuum the product exhibits a melting point of 94° C.

| Analysis | Calculated for $C_{18}H_{20}O_4N_3Cl$ | Found | |
|---|---|---|---|
| C% | 57.22 | 57.19 | 57.22 |
| H% | 5.30 | 5.36 | 5.45 |
| N% | 11.12 | 11.14 | 11.19 |

EXAMPLE 24

Preparation of N-[(4'-di-β-hydroxyethyl amino-2'-chloro) phenyl]-2-chloro-5-amino benzoquinoneimine.

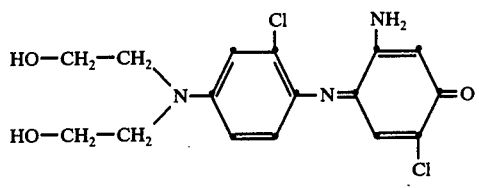

0.005 mole (1.40 g) of the hydrochloride of 3-chloro-4-nitroso-di-β-hydroxyethylaniline and 0.005 mole (0.72 g) of 2-chloro-5-amino phenol are introduced into 10 cc of a 1N sodium-hydroxide solution to which have been added 5 cc of ethanol (95°). The resulting reaction mixture is maintained for 2 hours with agitation at 40° C and then left to stand overnight at ambient temperature. The above indoaniline which precipitates is then filtered, washed with water and recyrstallized in a mixture of dimethylformamide and water. After drying under a vacuum, the product exhibits a melting point of 219° C.

| Analysis | Calculated for $C_{16}H_{17}N_3O_3Cl_2$ | Found | |
|---|---|---|---|
| C% | 51.89 | 51.72 | 51.68 |
| H% | 4.59 | 4.77 | 4.63 |
| N% | 11.35 | 11.27 | 11.25 |

EXAMPLE 25

Preparation of N-[(4'-di-β-hydroxyethyl amino-2'-chloro) phenyl]-2,6-dimethyl-3-amino benzoquinoneimine.

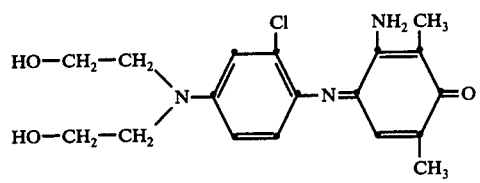

0.005 mole (1.40 g) of the hydrochloride of 3-chloro-4-nitroso-di-β-hydroxyethylaniline and 0.005 mole (0.87 g) of the hydrochloride of 2,6-dimethyl-3-amino phenol are introduced into 10 cc of a 1 N sodium hydroxide solution to which have been added 5 cc of ethyl alcohol (96°). The reaction mixture is agitated at 40° C for a period of 1 hour. After cooling, the above indoaniline which precipitates is filtered, first washed with a 50% hydroalcoholic solution and then with water, recrystallized in a mixture of dimethylformamide and water and dried under a vacuum. The product exhibits a melting point of 177° C.

| Analysis | Calculated for $C_{18}H_{22}N_3O_3Cl$ | Found | |
|---|---|---|---|
| C% | 59.42 | 59.28 | 59.36 |
| H% | 6.05 | 6.22 | 6.19 |
| N% | 11.55 | 11.43 | 11.50 |

EXAMPLE 26

Preparation of N-[(4'-ethyl,β-sulfoethyl amino-2'-methyl) phenyl]-2,6-dimethyl-3-amino benzoquinoneimine under the form of its ammonium salt.

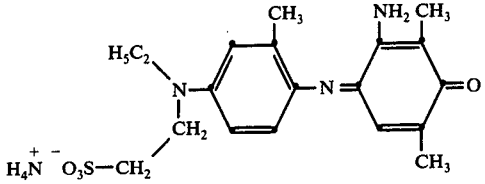

0.01 mole (1.73 g) of the hydrochloride of 2,6-dimethyl-3-amino phenol is introduced into 30 cc of a 50% hydroisopropopanolic solution to which have been added 10 cc of ammonia at 22° Be. There are then added with agitation 0.01 mole (2.58 g) of 4-N,N-(ethyl,β-sulfoethyl) amino-2-methyl aniline in 50 cc of water, and then, little by little, 0.011 mole (2.6 g) of ammonium persulfate in 10 cc of water. The resulting reaction mixture is left to stand overnight at 0° C. The above indoaniline which has crystallized in the form of its ammonium salt is then filtered. The thus recovered indoaniline is washed with a little water and then with acetone and subsequently dried under a vacuum. It melts with decomposition at 200° C. The product is chromatographically pure.

| Analysis | Calculated for $C_{19}H_{28}O_4N_4S$ | Found | |
|---|---|---|---|
| N% | 13.72 | 13.54 | 13.61 |
| S% | 7.83 | 7.69 | 7.59 |

EXAMPLE 27

Preparation of N-[(4'-di-β-hydroxyethyl amino) phenyl]-2-methyl-5-ureido benzoquinoneimine.

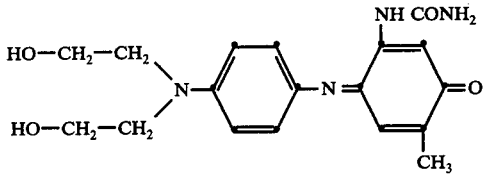

0.2 mole (33.2 g) of 2-methyl-5-ureido phenol and 0.22 mole (43.12 g) of N,N-di-β-hydroxyethyl paraphenylenediamine are dissolved in 500 cc of acetone to which have been added 200 cc of ammonia at 22° Bé. There are then added 500 g of crushed ice and little by little with agitation 0.4 mole (92 g) of ammonium persulfate in 300 cc of water. At the end of this addition, the reaction mixture is continued to be agitated for 30 minutes. There are then added 500 cc of acetone. The above indoaniline which precipitates is then filtered, washed with water and recrystallized in a mixture of dimethylformamide and water. The product is then dried under a vacuum at 60° C and exhibits a melting point of 186° C. It is again recrystallized and this time exhibits a melting point of 233° C.

| Analysis | Calculated for $C_{18}H_{22}N_4O_4$ | Found | |
|---|---|---|---|
| C% | 60.34 | 60.0 | 59.97 |
| H% | 6.14 | 6.21 | 6.24 |
| N% | 17.88 | 17.82 | 17.79 |

EXAMPLE 28

Preparation of N-[(4'-di-β-hydroxyethyl amino) phenyl]-2-methyl-5-amino benzoquinoneimine.

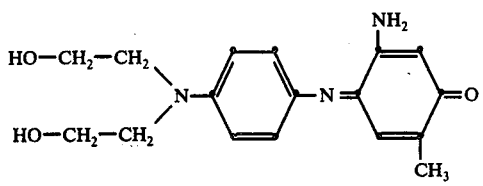

0.22 mole (54 g) of the hydrochloride of 4-nitroso-N,N-di-β-hydroxyethylaniline and 0.2 mole (24.6 g) of 2-methyl-5-amino phenol are dissolved in 720 cc of a 0.3 N sodium hydroxide solution to which have been added 200 cc of ethanol (96°). The solution is maintained with agitation for 1 hour at 50° C. The above indoaniline which precipitates is then filtered, washed with water and subsequently dried under a vacuum. The product melts at 107° C.

| Analysis | Calculated for $C_{17}H_{21}N_3O_3$ | Found | |
|---|---|---|---|
| C% | 64.76 | 64.48 | 64.57 |
| H% | 6.67 | 6.58 | 6.65 |
| N% | 13.33 | 13.12 | 13.36 |

EXAMPLE 29

Preparation of N-[(4'-di-β-hydroxyethyl amino) phenyl]-2,5-dimethyl benzoquinoneimine.

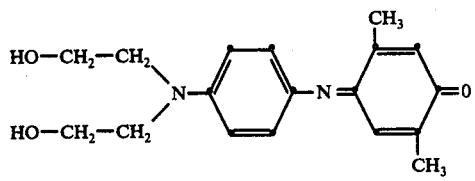

0.1 mole (12.2 g) of 2,5-xylenol and 0.1 mole (19.6 g) of N,N-di-β-hydroxyethyl paraphenylenediamine are dissolved in 300 cc of acetone to which have been added 100 cc of ammonia at 22° Bé. There are then added 300 g of crushed ice and little by little and with agitation 0.2 mole (45.6 g) of ammonium persulfate in 150 cc of water. The resulting reaction mixture is maintained with agitation for one hour at a temperature of about 0° C. The above indoaniline which precipitates is then filtered, washed with water, recrystallized in a mixture of dimethylformamide and water and dried under a vacuum. The product exhibits a melting point of 135° C.

| Analysis | Calculated for $C_{18}H_{22}N_2O_3$ | Found | |
|---|---|---|---|
| C% | 68.79 | 68.63 | 68.73 |
| H% | 7.01 | 7.17 | 7.05 |
| N% | 8.92 | 9.10 | 8.99 |

EXAMPLE 30

Preparation of N-[(4'-ethyl,β-morpholinoethyl amino) phenyl]-2,6-dimethyl-3-amino benzoquinoneimine.

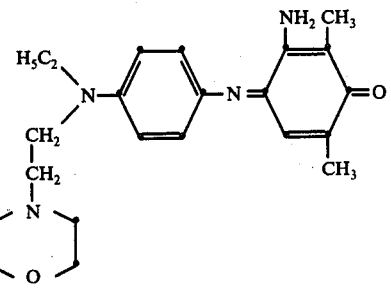

0.01 mole (33.6 g) of the dihydrochloride of 4-nitroso-N-ethyl-N-β-morpholinoethylaniline and 0.01 mole (1.73 g) of the hydrochloride of 2,6-dimethyl-3-amino phenol are dissolved in 40 cc of a 0.5 N sodium hydroxide solution. The reaction mixture is maintained for 2 hours with agitation at a temperature of 40° C. The above indoaniline which precipitates under the form of the monohydrochloride is then filtered. This monohydrochloride is treated for 30 minutes with agitation with 20 cc of a 2 N sodium hydroxide solution. The above indoaniline which precipitates is then filtered, washed with water and recrystallized in acetone. After drying under a vacuum, the product exhibits a melting point of 133° C.

| Analysis | Calculated for $C_{22}H_{30}O_2N_4$ | Found | |
|---|---|---|---|
| C% | 69.08 | 68.83 | 69.25 |
| H% | 7.91 | 8.02 | 8.10 |
| N% | 14.65 | 14.67 | 14.65 |

EXAMPLE 31

Preparation of N-[(4'-di-β-hydroxyethyl amino-2'-methoxy) phenyl]-2,6-dimethyl-3-amino benzoquinoneimine.

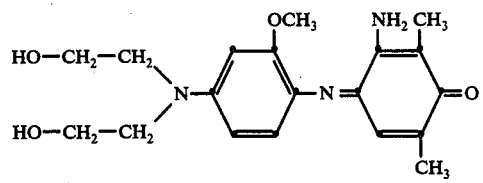

0.0275 mole (7.6 g) of the hydrochloride of 3-methoxy-4-nitroso-N,N-di-β-hydroxyethylaniline and 0.025 mole (4.34 g) of the hydrochloride of 2,6-dimethyl-3-amino phenol are introduced into 110 cc of a 1 N sodium hydroxide solution to which have been added 25 cc of ethanol. The resulting reaction mixture is maintained with agitation for 30 minutes at 50° C. After cooling, the above-identified indoaniline which has precipitated is then filtered, washed first with water and then with acetone. After drying under a vacuum, the product exhibits a melting point of 145° C and is chromatographically pure.

| Analysis | Calculated for $C_{19}H_{25}N_3O_4$ | Found | |
|---|---|---|---|
| C% | 63.50 | 63.12 | 63.24 |
| H% | 6.96 | 7.02 | 7.05 |
| N% | 11.69 | 11.65 | 11.59 |

EXAMPLE 32

Preparation of N-[(4'-morpholino) phenyl]2-methyl-5-amino benzoquinoneimine.

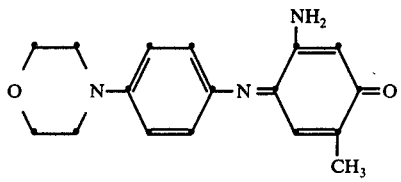

0.01 mole (1.78 g) of N-[4'-(amino)phenyl] morpholine and 0.01 mole (1.23 g) of 2-methyl-5-amino phenol are dissolved in 25 cc of water to which have been added 20 cc of acetone and 5 cc of ammonia at 22° Bé. To the resulting solution, there is then added, little by little, with agitation and while maintaining the temperature at about 0° C, 0.02 mole (4.6 g) of ammonium persulfate in 40 cc of water. At the end of this addition, the reaction mixture is continued to be agitated for 10 minutes. The above indoaniline which has precipitated is then filtered, washed with water and subsequently recrystallized in acetone. After drying under a vacuum, the product exhibits a melting point of 244° C.

| Analysis | Calculated for $C_{17}H_{19}N_3O_2$ | Found | |
|---|---|---|---|
| C% | 68.66 | 68.45 | 68.73 |
| H% | 6.44 | 6.47 | 6.42 |
| N% | 14.13 | 14.26 | 14.19 |

EXAMPLE 33

Preparation of N-[(4'-morpholino) phenyl]-2,6-dimethyl-3-amino benzoquinoneimine.

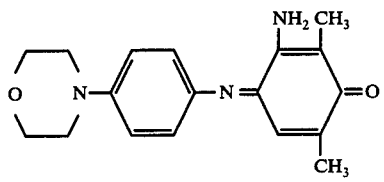

0.01 mole (1.78 g) of N-[4'-(amino) phenyl] morpholine and 0.01 mole (1.74 g) of the hydrochloride of 2,6-dimethyl-3-amino phenol are dissolved in 40 cc of water to which have been added 18 cc of ammonia at 22° Be. To the resulting solution there is added, little by little with agitation, while maintaining the temperature of the reaction mixture near 15° C, 0.01 mole (2.3 g) of ammonium persulfate in 15 cc of water. At the end of this addition, the agitation of the reaction mixture is continued for 20 minutes. The above indoaniline which has precipitated is filtered, washed with water and recrystallized in a mixture of dimethylformamide and water. The product is then dried under a vacuum and exhibits a melting point of 206° C.

| Analysis | Calculated for $C_{18}H_{21}N_3O_2$ | Found | |
|---|---|---|---|
| C% | 69.43 | 69.46 | 69.27 |
| H% | 6.80 | 6.82 | 7.01 |
| N% | 13.50 | 13.59 | 13.69 |

EXAMPLE 34

Preparation of N-[(4'-piperidino) phenyl]-2-methyl-5-amino benzoquinoneimine.

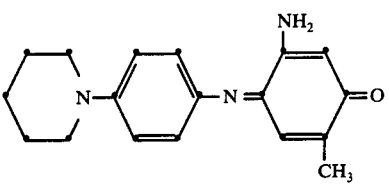

0.01 mole (2.25 g) of the sulfate of N-[4'-(amino)phenyl] piperidine and 0.01 mole (1.23 g) of 2-methyl-5-amino phenol are dissolved in 40 cc of a 50% hydroacetonic solution to which have been added 10 cc of ammonia at 22° Bé. To the resulting solution there is added, little by little, with agitation, and while maintaining the temperature near 0° C, 0.02 mole (4.6 g) of ammonium persulfate in 40 cc of water. At the termination of this addition, the agitation of the reaction mixture is continued for 10 minutes. The above indoaniline which has precipitated is then filtered, washed with water and recrystallized in a mixture of dimethylformamide and water. After drying under a vacuum the product exhibits a melting point of 208° C.

| Analysis | Calculated for $C_{18}H_{21}N_3O$ | Found | |
|---|---|---|---|
| C% | 73.19 | 72.98 | 73.06 |
| H% | 7.17 | 6.96 | 7.06 |
| N% | 14.23 | 14.31 | 14.40 |

EXAMPLE 35

Preparation of N-[(4'-ethyl,carbamylmethyl amino-2'-methyl) phenyl]-3-ureido benzoquinoneimine.

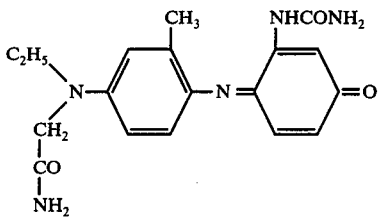

0.04 mole (6.08 g) of 3-ureido phenol is dissolved in 200 cc of isopropyl alcohol to which have been added 200 cc of ammonia at 22° Bé. Further, 0.044 mole (9.2 g) of 2-methyl-4-N-(ethyl,carbamylmethyl) amino aniline is dissolved in 40 cc of water to which have been added 10 cc of hydrochloric acid ($d = 1.18$). These two solutions are then mixed together and there are added thereto 330 g of ice. To the resulting ice solution there is introduced, little by little with agitation, while maintaining the temperature thereof near 0° C, 0.088 mole (20.2 g) of ammonium persulfate in 60 cc of water. At the end of this addition, the above raw indoaniline which has precipitated is then filtered, and washed with water. After recrystallization in a mixture of dimethylformamide and water and drying under a vacuum, the product exhibits a melting point of 234° C.

| Analysis | Calculation for $C_{18}H_{21}O_3N_5$ | Found | |
|---|---|---|---|
| C% | 60.84 | 60.65 | 60.72 |
| H% | 5.91 | 6.12 | 6.00 |
| N% | 19.71 | 19.92 | 19.86 |

EXAMPLE 36

Preparation of N-[(4'-ethyl,β-mesylaminoethyl amino) phenyl]-2,6-dimethyl-3-acetylamino benzoquinoneimine.

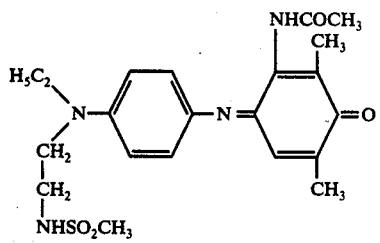

0.01 mole (2.57 g) of 4-N-(ethyl,β-mesylaminoethyl) amino aniline and 0.01 mole (1.79 g) of 2,6-dimethyl-3-acetylamino phenol are dissolved in 30 cc of a 50% hydroacetonic solution to which have been added 15 cc of ammonia at 22° Bé. The resulting reaction mixture is cooled to 0° C and there is then added, little by little with agitation 0.02 mole (4.6 g) of ammonium persulfate in 15 cc of water. At the end of this addition, the agitation of the reaction mixture is continued for 15 minutes, at which point there are added 30 cc of acetone. After several hours of cooling to 0° C, the above indoaniline crystallizes and is then filtered from the reaction mixture, washed with water and recrystallized in hydroacetonic medium. After drying under a vacuum, the product exhibits a melting point of 130° C.

| Analysis | Calculated for $C_{21}H_{28}N_4O_4S$ | Found | |
|---|---|---|---|
| C% | 58.32 | 58.18 | 58.34 |
| H% | 6.53 | 6.71 | 6.64 |
| N% | 12.96 | 12.93 | 12.76 |
| S% | 7.40 | 7.33 | 7.38 |

EXAMPLE 37

Preparation of N-[(4'-di-β-hydroxyethyl amino-2'-methyl) phenyl]-2,6-dimethyl-3-amino benzoquinoneimine.

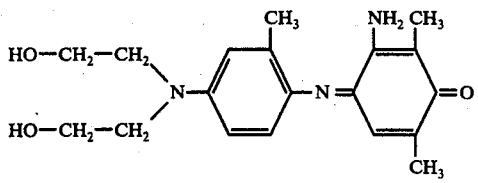

Into 20 cc of a 1 N sodium hydroxide solution to which have been added 20 cc of ethanol, there are introduced with agitation and at ambient temperature, 0.02 mole (5.20 g) of the hydrochloride of 3-methyl-4-nitroso-N,N-di-β-hydroxyethylaniline and 0.02 mole (3.46 g) of the hydrochloride of 2,6-dimethyl-3-amino phenol. The resulting reaction mixture is continued to be agitated for 5 hours at which point the above indoaniline which precipitates is filtered, washed with water and subsequently recrystallized in a mixture of dimethylformamide and water. The thus recovered indoaniline is dried under a vacuum and exhibits a melting point of 195° C.

| Analysis | Calculated for $C_{19}H_{25}N_3O_3$ | Found | |
|---|---|---|---|
| C% | 66.45 | 66.22 | 65.98 |
| H% | 7.34 | 7.20 | 7.39 |
| N% | 12.24 | 11.98 | 12.17 |

EXAMPLE 38

Preparation of N-[(4'-ethyl-β-sulfoethyl amino)-phenyl]-2,6-dimethyl-3-amino benzoquinoneimine in the form of its ammonium salt.

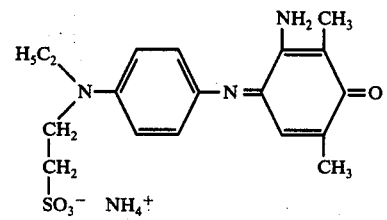

To a suspension of 0.05 mole (12.9 g) of 4-nitroso-N,N-(ethyl-β-sulfoethyl) aniline and 0.05 mole (8.65 g) of the hydrochloride of 2,6-dimethyl-3-amino phenol in 100 cc of iced water, there are added, little by little, with agitation, 10 cc of ammonia at 22° Bé. The resulting reaction mixture is then left to stand for 2 hours at 20° C with agitation. There are then added sufficient ammonia at 22° Bé to achieve a pH of 11 and sufficient ammonium chloride thereto to effect saturation. After cooling for several hours at −5° C the above indoaniline crystallizes under the form of its ammonium salt. The indoaniline is filtered, washed with a little ice water and then with acetone and subsequently dried under a vacuum. It melts with decomposition at 225° C.

| Analysis | Calculated for $C_{18}H_{26}N_4O_4S$ | Found | |
|---|---|---|---|
| N% | 14.21 | 14.51 | 14.38 |
| S% | 8.12 | 7.86 | 7.92 |

EXAMPLE 39

Preparation of N-[(4'-ethyl,β-piperidinoethyl amino) phenyl]-3-chloro-6-acetylamino benzoquinoneimine.

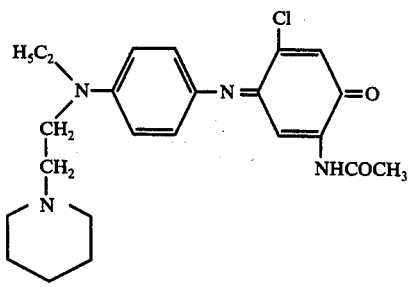

0.01 mole (1.85 g) of 3-chloro-6-acetylamino phenol is dissolved in 12 cc of a 50% hydroacetonic solution to which have been added 20 cc of ammonia at 22° Bé. To this solution, cooled to 0° C, there are added, little by little and simultaneously with the aid of a double funnel, 0.02 mole (4.60 g) of ammonium persulfate in 20 cc of water, and 0.01 mole (3.56 g) of the trihydrochloride of 4-N-(ethyl,-β-piperidino ethyl) amino aniline in 20 cc of water. At the termination of these additions, the reaction mixture is continued to be agitated for 10 minutes at which point the above indoaniline which has precipitated is filtered, washed with water and recrystallized in a hydroacetonic mixture. After drying under a vacuum the product exhibits a melting point of 96° C.

| Analysis | Calculated for $C_{23}H_{29}N_4ClO_2$ | Found | |
|---|---|---|---|
| C% | 64.41 | 64.63 | 64.52 |
| H% | 6.80 | 6.91 | 6.90 |
| N% | 13.06 | 13.02 | 13.03 |
| Cl% | 8.29 | 8.46 | 8.35 |

EXAMPLE 40

Preparation of N-[(4'-morpholino) phenyl]-2-chloro-5-acetylamino benzoquinoneimine.

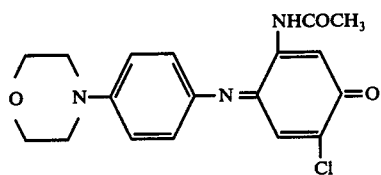

0.01 mole (1.78 g) of N-[(4'-(amino) phenyl] morpholine is dissolved in 20 cc of water to which have been added 10 cc of isopropanol. Further 0.01 mole (1.85 g) of 2-chloro-5-acetylamino phenol is dissolved in 25 cc of a 2 N sodium hydroxide solution. The resulting two solutions are mixed together and there is added thereto, little by little with agitation, and while maintaining the temperature thereof near 0° C, 0.01 mole (2.3 g) of ammonium persulfate in 10 cc of water. At the end of this addition, the reaction mixture is continued to be agitated for 10 minutes at which point the above indoaniline which precipitates is then filtered, washed with water and then with acetone and subsequently dried under a vacuum thereby producing a product exhibiting a melting point of 227° C.

| Analysis | Calculated for $C_{18}H_{18}Cl\,N_3O_3$ | Found | |
|---|---|---|---|
| C% | 60.08 | 59.84 | 60.00 |
| H% | 5.04 | 5.17 | 5.24 |
| N% | 11.68 | 11.57 | 11.47 |
| Cl% | 9.86 | 10.12 | 10.16 |

EXAMPLE 41

Preparation of N-[(4'-ethyl, carbamylmethyl amino) phenyl]-2,6-dimethyl benzoquinoneimine.

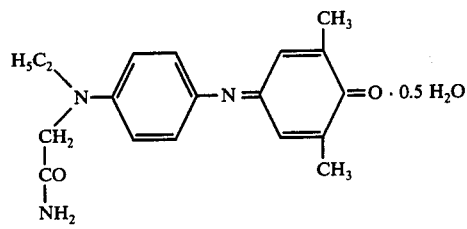

0.02 mole (2.44 g) of 2,6-dimethyl phenol and 0.02 mole (3.86 g) of 4-amino-N-(ethyl,carbamylmethyl) aniline are dissolved in 60 cc of a 50% hydroacetonic solution to which have been added 30 cc of ammonia (22° Bé). To the resulting solution, cooled to a temperature between 0°–5° C, there is added, little by little, with agitation, 0.04 mole (9.2 g) of ammonium persulfate in 30 cc of water. At the end of this addition, the stirring of the reaction mixture is continued for 30 minutes at about +5° C. The above indoaniline which precipitates in the form of crystals is then filtered, washed with water and recrystallized in a mixture of dimethylformamide and water. After drying under a vacuum the product melts at 88° C, it is taken up again and melts at 146° C.

| Analysis | Calculated for $C_{18}H_{21}N_3O_2\,0.5\,H_2O$ | Found |
|---|---|---|
| C% | 67.56 | 67.82 |
| H% | 6.93 | 6.75 |
| N% | 13.13 | 13.13 |

EXAMPLE 42

Preparation of N-[(4'-ethyl, carbamylmethylamino) phenyl]-3,6-dimethyl benzoquinoneimine.

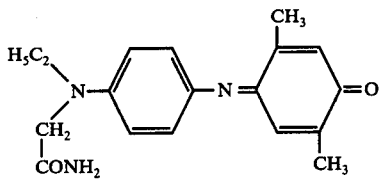

0.02 mole (2.44 g) of 2,5-dimethyl phenol and 0.02 mole (3.86 g) of 4-amino-N,N-(ethyl,carbamylmethyl) aniline are dissolved in 25 cc of acetone, 20 cc of water and 25 cc of ammonia (22° Bé). To the resulting solution, maintained at a temperature of about +5° C, there is added, little by little, with agitation, 0.04 mole (9.2 g) of ammonium persulfate dissolved in 30 cc of water. At the end of this addition, the stirring of the reaction mixture is continued for 15 minutes. The above indoaniline which precipitates is then filtered, washed first with water and then with a little dimethylformamide and finally with water. After drying under a vacuum at 100° C, the product exhibits a melting point of 176° C.

| Analysis | Calculated for $C_{18}H_{21}N_3O_2$ | Found |
|---|---|---|
| C% | 69.43 | 69.33 |
| H% | 6.80 | 7.04 |
| N% | 13.50 | 3.63 |

EXAMPLE 43

Preparation of N-[(4'-ethyl,β-mesylaminoethyl amino-2'-methyl) phenyl]-2,3-dimethyl benzoquinoneimine.

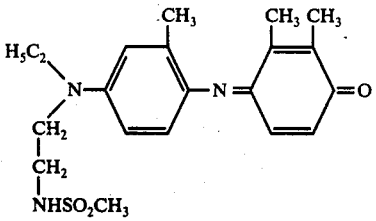

0.02 mole (2.44 g) of 2,3-xylenol and 0.02 mole (5.42 g) of 3-methyl-4-amino-N,N-(ethyl, β-mesylaminoethyl) aniline are dissolved in 100 cc of a 50% hydroacetonic solution to which have been added 10 cc of ammonia (22° Bé). To the resulting solution, cooled to 0° C, there is added, little by little, with agitation 0.04 mole (9.2 g) of ammonium persulfate dissolved in 50 cc of water. At the end of this addition, the stirring of the reaction mixture is continued for a few minutes. The above indoaniline which has precipitated is then filtered, washed with water, recrystallized in a mixture of dimethylformamide and water and dried under a vacuum. It melts at 154° C.

| Analysis | Calculated for $C_{20}H_{27}N_3SO_3$ | Found |
|---|---|---|
| C% | 61.68 | 61.79 |
| H% | 6.99 | 7.18 |
| N% | 10.79 | 1.90 |
| S% | 8.21 | 8.45 |

EXAMPLE 44

Preparation of N-[(4'-ethyl,carbamylmethyl amino) phenol]-3-ureido benzoquinoneimine.

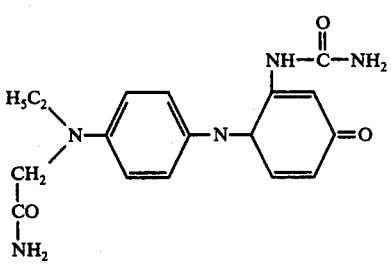

0.02 mole (3.86 g) of 4-amino-N-(ethyl, carbamylmethyl) aniline and 0.02 mole (3 g) of 3-ureido phenol are dissolved in 100 cc of a 50% hydroacetonic solution to which have been added 25 cc of ammonia (22° Bé). To the resulting solution, cooled to 0° C, there is added, little bylittle with agitatin, 0.04 mole (9.2 g) of ammonium persulfate in solution in 40 cc of water. At the end of this addition the stirring of the reaction mixture is continued for 15 minutes. The above indoaniline which has precipitated in the form of crystals is then filtered, washed with water, recrystallized in a mixture of dimethylformamide and water and dried under a vacuum. It melts at 252° C.

| Analysis | Calculated for $C_{17}H_{19}N_5O_3$ | Found |
|---|---|---|
| C% | 59.81 | 59.79 |
| H% | 5.61 | 5.82 |
| N% | 20.52 | 20.45 |

EXAMPLE 45

Preparation of N-[(4'-di-β-hydroxyethylamino-2'-methoxy) phenyl]-6-methyl-3-amino benzoquinoneimine.

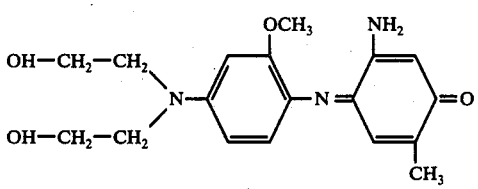

0.02 mole (5.5 g) of the hydrochloride of 3-methoxy-4-nitroso-N,N-di-β-hydroxyethylaniline is dissolved in 50 cc of water. Further, 0.02 mole (2.46 g) of 2-methyl-5-amino phenol is dissolved in 10 cc of ethanol to which have been added 20 cc of a 1 N NaOH solution. The two solutions are mixed together and the resulting mixture is agitated for 30 minutes at 50° C. The above indoaniline which precipitates in the form of crystals is then filtered, washed with water at 50° C, recrystallized in a mixture of dimethylformamide and dried under a vacuum. It melts at 180° C.

| Analysis | Calculated for $C_{18}H_{23}N_3O_4$ | Found |
|---|---|---|
| C% | 62.59 | 62.21 |
| H% | 6.71 | 6.97 |
| N% | 12.17 | 12.15 |

EXAMPLE 46

Preparation of N-[(4'-di-β-hydroxyethylamino-2'-methoxy)phenyl]-6-methyl-3-carbamylmethylamino benzoquinone imine.

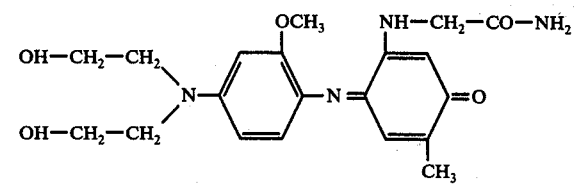

0.1 mole (28 g) of the hydrochloride of 3-methoxy-4-nitroso-N,N-di-β-hydroxyethyl aniline is dissolved in 100 cc of water. Further, 0.1 mole (18 g) of 2-methyl-5-carbamylmethylamino phenol is dissolved in 100 cc of ethanol to which have been added 100 cc of a 1.2 N NaOH solution. The two solutions are then mixed together and the temperature of the resulting mixture is maintained for 30 minutes at 45° C. After cooling, the above indoaniline which precipitates is then filtered, washed with water and dried under a vacuum. It melts at 210° C.

| Analysis | Calculated for $C_{20}H_{26}N_4O_5$ | Found |
|---|---|---|
| C% | 59.69 | 59.56 |
| H% | 6.51 | 6.32 |
| N% | 13.92 | 14.09 |

EXAMPLE 47

Preparation of N-[(4'-ethyl,β-mesylaminoethyl) amino) phenyl]-6-methyl-3-carbamylmethylamino benzoquinoneimine.

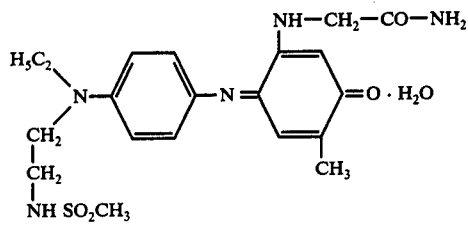

0.01 mole (1.8 g) of 2-methyl-5-carbamylmethylamino phenol and 0.01 mole (2.57 g) of 4-amino-N-(ethyl,β-mesylaminoethyl) aniline are dissolved in 20 cc of acetone, 15 cc of water and 15 cc of ammonia (22° Bé). To the resulting solution, cooled to 0° C, there is added, little by little, with agitation, 0.02 mole (4.6 g) of ammonium persulfate in 15 cc of water. At the end of this addition, the stirring of the reaction mixture is continued for 30 minutes at about 15° C. The above indoaniline which has precipitated in the form of crystals is then filtered, washed with water, recrystallized in a mixture of dimethylformamide and water and dried under a vacuum. It melts at 134° C.

| Analysis | Calculated for $C_{20}H_{27}N_5O_4S \cdot H_2O$ | Found |
|---|---|---|
| C% | 53.21 | 53.22 |
| H% | 6.43 | 6.43 |
| N% | 15.52 | 15.67 |
| S% | 7.09 | 7.29 |

EXAMPLE 48

Preparation of N-[(4'-ethyl,β-mesylaminoethylamino) phenyl]-6-methyl-2-β-hydroxyethylamino benzylquinoneimine.

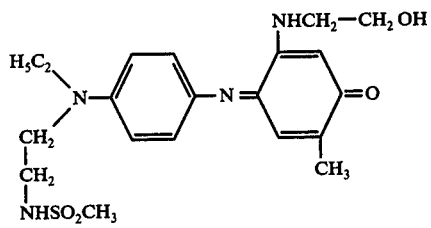

0.01 mole (1.67 g) of 2-methyl-5-β-hydroxyethylamino phenol and 0.088 mole (2.39 g) of 4-nitroso-N,N-(ethyl,β-mesylaminoethyl) aniline are dissolved in 15 cc of ethyl alcohol at 95° C. The resulting mixture is maintained for 24 hours with agitation at a temperature of about 40° C. After cooling, the above indoaniline which has precipitated is filtered. The raw product is then washed with a 50% hydroethanolic solution and recrystallized in a mixture of dimethylformamide and water. It is dried under a vacuum and exhibits a melting point of 128° C.

| Analysis | Calculated for $C_{20}H_{28}N_4O_4S$ | Found |
|---|---|---|
| C% | 57.14 | 56.84 |
| H% | 6.66 | 6.77 |
| N% | 13.33 | 13.19 |
| S% | 7.61 | 7.97 |

EXAMPLE 49

Preparation of N-[(4'-ethyl,carbamylmethylamino)-phenyl]-6-methyl-3-carbethoxyamino benzoquinoneimine

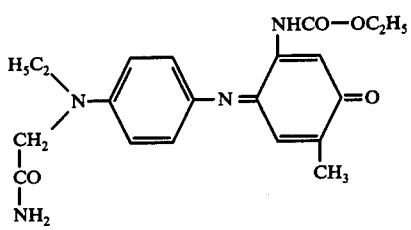

0.01 mole (1.65 g) of 4-amino-N,N-ethyl, carbamylmethyl) aniline and 0.01 mole (1.95 g) of 2-methyl-5-carbethoxyamino phenol are dissolved in 50 cc of a 50% hydroacetonic solution to which have been added 12 cc of ammonia (22° Bé). To the resulting solution, cooled to 0° C, there is added, little by little, with agitation, 0.02 mole (4.6 g) of ammonium persulfate dissolved in 20 cc of water. At the end of this addition, the stirring of the reaction mixture is continued for 20 minutes. The above indoaniline which has precipitated is then filtered, washed first with water and then with acetone, recrystallized in a mixture of dimethylformamide and water and dried under a vacuum. It melts at 210° C.

| Analysis | Calculated for $C_{20}H_{24}N_4O_4$ | Found |
|---|---|---|
| C% | 62.48 | 62.33 |
| H% | 6.29 | 6.21 |
| N% | 14.58 | 14.74 |

EXAMPLE 50

Preparation of N-[(4'-ethyl,β-mesylaminoethylamino) phenyl]-6-methyl-3-acetylamino benzoquinoneimine.

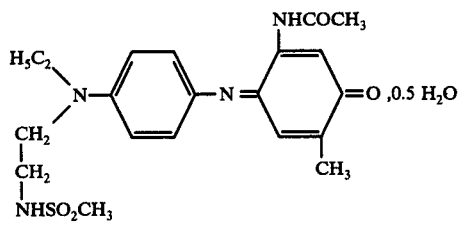

0.01 mole (1.65 g) of 2-methyl-5-acetylamino phenol and 0.01 mole (2.57 g) of 4-amino-N,N-(ethyl, mesylaminoethyl) aniline are dissolved in 40 cc of a 50% hydroacetonic solution to which have been added 15 cc of ammonia (22° Bé). To the resulting solution, there is added, little by little, with agitation and while maintaining the temperature at about +5° C, 0.02 mole (4.6 g) of ammonium persulfate dissolved in 20 cc of water. At the end of this addition, the stirring of the reaction mixture is continued for 30 minutes. The above indoaniline which has precipitated in the form of crystals is then filtered, washed with water, recrystallized in a mixture of dimethylformamide and water and dried under a vacuum at 100° C. It melts at 163° C.

| Analysis | Calculated for $C_{20}H_{26}N_4O_4S \cdot 0.5 H_2O$ | Found |
|---|---|---|
| C% | 56.20 | 56.48 |
| H% | 6.32 | 6.15 |
| N% | 13.11 | 13.14 |
| S% | 7.49 | 7.64 |

EXAMPLE 51

Preparation of N-[(4'-ethyl,carbamylmethylamino)phenyl]-6-methyl-3-acetylamino benzoquinoneimine.

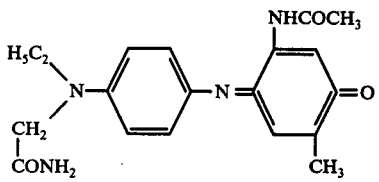

0.02 mole (3.86 g) of 4-amino-N,N-(ethyl, carbamylmethyl) aniline and 0.02 mole (3.3 g) of 2-methyl-5-acetylamino phenol are dissolved in 100 cc of a 50% hydroacetonic solution to which have been added 25 cc of ammonia (22° Bé). To the resulting solution, cooled to 0° C, there is added, little by little, with agitation, 0.04 mole (9.2 g) of ammonium persulfate dissolved in 40 cc of water. At the end of this addition, the stirring of the reaction mixture is continued for 10 minutes. The above indoaniline which has precipitated is then filtered, recrystallized in dimethylformamide and dried under a vacuum. It melts at 252° C.

| Analysis | Calculated for $C_{19}H_{22}N_4O_3$ | Found |
|---|---|---|
| C% | 64.39 | 64.15 |
| H% | 6.26 | 6.29 |
| N% | 15.81 | 15.55 |

EXAMPLE 52

Preparation of N-[(4'-di-β-hydroxyethylamino)phenyl]-6-methyl-3-carbamylmethylamino benzoquinone.

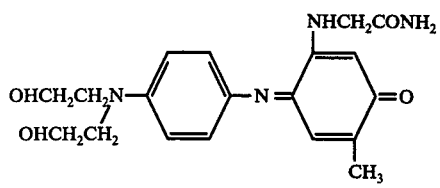

0.1 mole (17.9 g) of 2-methyl-5-carbamylmethylamino phenol is dissolved in 220 cc of a 50% hydroethanolic normal NaOH solution. To this solution there is added 0.11 mole (27.1 g) of the hydrochloride of 4-nitroso-N,N-(di-β-hydroxyethyl)aniline dissolved in 250 cc of water at 50° C. The resulting reaction mixture is maintained with agitation for 1 hour at 50° C. The above indoaniline which precipitates is then filtered, washed with water, recrystallized in a mixture of dimethylformamide and water and dried under a vacuum. It melts at 205° C.

| Analysis | Calculated For $C_{19}H_{24}N_4O_4$ | | Found |
|---|---|---|---|
| C% | 61.29 | 61.02 | 60.98 |
| H% | 6.45 | 6.57 | 6.62 |
| N% | 15.05 | 15.27 | 15.31 |

EXAMPLE 53

Preparation of N-[(4'-ethyl-β-sulfoethyl amino-2'-methyl)phenyl]-2,6-dimethyl-3-acetylamino benzoquinoneimine in the form of its ammonium salt

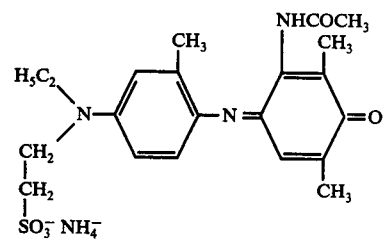

0.01 mole (1.79 g) of 2,6-dimethyl-5-acetylamino phenol and 0.01 mole (2.58 g) of 4-amino-3-methyl-N,N-ethyl,β-sulfoethylaniline are dissolved in 30 cc of isopropanol, 50cc of water and 12 cc of ammonia (22° Bé). To the resulting solution there is added, little by little, at a temperature of about 15° C, 0.11 mole (2.56 g) of ammonium persulfate dissolved in 10 cc of water. The reaction mixture is then left to stand for 24 hours at ambient temperature at which time it is then cooled to 0° C for a period of 2 days. The above indoaniline which precipitates in the form of its ammonium salt is then filtered, washed first with a little ice water and then with acetone and dried under a vacuum. The product which melts with decomposition at 205° C, is chromatographically pure.

| Analysis | Calculated For $C_{21}H_{30}N_4O_5S$ | Found |
|---|---|---|
| S% | 7.10 | 7.22 |

EXAMPLE 54

Preparation of N-[(4'-ethyl,carbamylmethylamino)phenyl]-2,6-dimethyl-3-acetylamino benzoquinoneimine

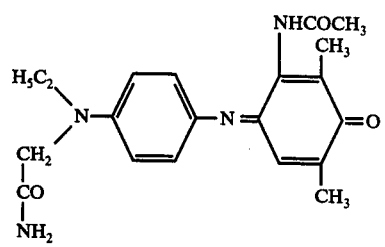

0.1 mole (17.9 g) of 2,6-dimethyl-5-acetylamino phenol and 0.11 mole (21.2 g) of 4-amino-N,N-ethyl,carbamylmethyl aniline are dissolved in 500 cc of isopropanol, 900 cc of water and 500 cc of ammonia (22° Bé). To the resulting solution, maintained at a temperature of about +5° C, there is added 0.22 mole (51 g) of ammonium persulfate dissolved in 150 cc of water. At the end of this addition, the stirring of the reaction mixture is continued for 45 minutes. The above indoaniline which has precipitated in the form of crystals is then filtered, washed first with water and then with acetone, and dried under a vacuum. It melts at 222° C.

| Analysis | Calculated For $C_{20}H_{24}N_4O_3$ | Found |
|---|---|---|
| C% | 65.22 | 65.22 |
| H% | 6.52 | 6.78 |
| N% | 15.22 | 15.10 |

EXAMPLE 55

Preparation of N-[(4'-methyl,β-hydroxyethylamino-3'-methyl)phenyl]-3-ureido benzoquinoneimine.

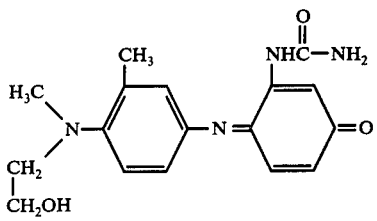

0.01 mole (1.52 g) of 3-ureido phenol is dissolved in 25 cc of acetone to which have been added 25 cc of ammonia (22° Bé). To the resulting solution, cooled in ice there are added, little by little, with agitation and simultaneously with the aid of a double funnel, 0.01 mole (2.77 g) of the sulfide of 2-methyl-4-amino-N,N-methyl,β-hydroxyethyl aniline dissolved in 25 cc of water and 0.02 mole (4.6 g) of ammonium persulfate dissolved in 40cc of water. At the end of these additions, the stirring of the reaction mixture is continued for 1 hour at a temperature of about +5° C. The above indoaniline which precipitates is then filtered, washed with ethyl alcohol (95°), recrystallized in ethylacetate and dried under a vacuum. It melts at 205° C.

| Analysis | Calculated For $C_{17}H_{20}N_4O_3$ | Found |
|---|---|---|
| C% | 62.18 | 61.95 |
| H% | 6.14 | 6.28 |
| N% | 17.06 | 17.19 |

EXAMPLES OF USE

Part A - Examples of Hair Setting Lotions

| a1) | Dye of Example 10 | 0.1 g |
|---|---|---|
| | Polyvinylpyrrolidone - M.W. 40,000 | 2.5 g |
| | Ethyl alcohol (96°) | 30 g |
| | Triethanolamine, q.s.p. pH 7 | |
| | Water, q.s.p. | 100 g |

This composition when applied as a hair setting lotion to bleached hair imparts thereto a pale pearly glycine shade.

| a2) | Dye of Example 4 | 0.05 g |
|---|---|---|
| | Copolymer of vinylpyrrolidone/ vinyl acetate 60/40, M.W. 80,000 to 120,000 | 2 g |
| | Ethyl alcohol (96°) | 20 g |
| | Triethanolamine, q.s.p. pH 9.5 | |
| | Water, q.s.p. | 100 g |

This composition when applied as a hair setting lotion to bleached hair imparts thereto a bright pearly-grey shade.

| a3) | Dye of Example 6 | 0.2 g |
|---|---|---|
| | Copolymer of vinylpyrrolidone/ vinyl acetate, 70/30, M.W. 40,000 | 1.5 g |
| | Isopropyl alcohol | 35 g |
| | Triethanolamine, q.s.p. pH 6 | |
| | Water, q.s.p. | 100 g |

This composition when applied as a hair setting lotion to bleached hair imparts thereto a lightly metallic blue-grey coloration.

| a4) | Dye of Example 8 | 0.05 g |
|---|---|---|
| | Copolymer of vinylpyrrolidone/ vinyl acetate, 30/70, M.W. 60,000 | 3 g |
| | Ethyl alcohol (96°) | 45 g |
| | Triethanolamine, q.s.p. pH 8 | |
| | Water, q.s.p. | 100 g |

This composition when applied as a hair setting lotion to bleached hair imparts thereto an ash blond coloration with mauve glints.

| a5) | Dye of Example 3 | 0.05 g |
|---|---|---|
| | Copolymer of vinylpyrrolidone/ vinyl acetate 60/40, M.W. 80,000 to 120,000 | 1 g |
| | Isopropyl alcohol | 25 g |
| | Triethanolamine, q.s.p. pH 10 | |
| | Water, q.s.p. | 100.00 g |

This composition when applied as a hair setting lotion to bleached hair imparts thereto a rose blonde coloration.

| a6) | Dye of Example 11 | 0.05 g |
|---|---|---|
| | Copolymer of vinylpyrrolidone/ vinyl acetate, 70/30, M.W. - 40,000 | 3 g |
| | Ethyl alcohol (96°) | 45 g |
| | Triethanolamine, q.s.p. pH 10.2 | |
| | Water, q.s.p. | 100 g |

This composition when applied as a hair setting lotion to bleached hair imparts thereto a sea-green coloration with golden glints

| a7) | Dye of Example 2 | 0.06 g |
|---|---|---|
| | Copolymer of vinylpyrrolidone/ vinyl acetate, 30/70, M.W. 160,000 | 2.75 g |
| | Isopropyl alcohol | 20 g |
| | Triethanolamine, q.s.p. pH 8 | |
| | Water, q.s.p. | 100 g |

This composition when applied as a hair setting lotion to bleached hair imparts thereto a purplish ultramarine blue coloration.

| a8) | Dye of example 7 | 0.08 g |
|---|---|---|
| | Terpolymer of methyl methacrylate/ stearyl methacrylate/dimethyl methacrylate - 20/23/57 (made in accordance with SN 287845 filed 11-9-1972) | 2 g |
| | Ethyl alcohol (96°) | 35 g |
| | Triethanolamine, q.s.p. pH 8.5 | |

-continued

| | | |
|---|---|---|
| Water q.s.p. | | 100 g |

This composition when applied as a hair setting lotion to bleached hair imparts thereto a light silvery turquoise coloration.

| a9) | Dye of example 5 | 0.16 g |
|---|---|---|
| | Copolymer of vinylpyrrolidone/ vinyl acetate, 60/40, M.W. 80,000 to 120,000 | 2.25 g |
| | Isopropyl alcohol | 30 g |
| | Triethanolamine, q.s.p. pH 9 | |
| | Water, q.s.p. | 100 g |

This composition when applied as a hair setting lotion to bleached hair imparts thereto a bright steel-grey coloration.

| a10) | Dye of example 1 | 0.25 g |
|---|---|---|
| | Copolymer of vinyl acetate/ crotonic acid, 90/10, M.W. 45,000 - 50,000 | 2 g |
| | Ethyl alcohol (96°) | 50 g |
| | Triethanolamine, q.s.p. pH 5.5 | |
| | Water, q.s.p. | 100 g |

This composition when applied as a hair setting lotion to bleached hair imparts thereto a pearly parme coloration.

| a11) | Dye of example 13 | 0.1 g |
|---|---|---|
| | Copolymer of vinylpyrrolidone/ vinyl acetate, 30/70, M.W. 160,000 | 2.5 g |
| | Ethyl alcohol (96°) | 25 g |
| | Triethanolamine, q.s.p. pH 7.5 | |
| | Water q.s.p. | 100 g |

This composition when applied as a hair setting lotion to bleached hair imparts thereto a brilliant pale sandlewood coloration.

| a12) | Dye of example 9 | 0.05 g |
|---|---|---|
| | Polyvinylpyrrolidone, M.W. 40,000 | 1 g |
| | Isopropyl alcohol | 20 g |
| | Triethanolamine, q.s.p. pH 7 | |
| | Water, q.s.p. | 100 g |

This composition when applied as a hair setting lotion to bleached hair imparts thereto a parme coloration with silvery glints.

| a13) | Dye of example 12 | 0.2 g |
|---|---|---|
| | Copolymer of vinylpyrrolidone/ vinyl acetate, 30/70, M.W. 160,000 | 2 g |
| | Ethyl alcohol (96°) | 50 g |
| | Triethanolamine, q.s.p. pH 9.5 | |
| | Water, q.s.p. | 100 g |

This composition when applied as a hair setting lotion to bleached hair imparts thereto a metallic violet-grey coloration.

| a14) | Dye of example 14 | 0.15 g |
|---|---|---|
| | Copolymer of vinylpyrrolidone/ vinyl acetate, 60/40, M.W. 80,000 to 120,000 | 2 g |
| | Ethyl alcohol (96°) | 35 g |
| | Triethanolamine, q.s.p. pH 8.5 | |
| | Water, q.s.p. | 100 g |

This composition when applied as a hair setting lotion to bleached hair imparts thereto a duck-blue coloration.

| a15) | Dye of example 15 | 0.05 g |
|---|---|---|
| | Copolymer of vinylpyrrolidone/ vinyl acetate, 60/40, M.W. 80,000 to 120,000 | 2.5 g |
| | Ethyl alcohol (96°) | 30 g |
| | Triethanolamine, q.s.p. pH 6.5 | |
| | Water, q.s.p. | 100 g |

This composition when applied as a hair setting lotion to bleached hair imparts thereto a slate blue coloration.

| a16) | Dye of example 16 | 0.2 g |
|---|---|---|
| | vinylpyrrolidone, M.W. 40,000 | 2 g |
| | Isopropyl alcohol | 50 g |
| | Triethanolamine, q.s.p. pH 7 | |
| | Water, q.s.p. | 100 g |

This composition when applied as a hair setting lotion to bleached hair imparts thereto a blue coloration.

| a17) | Dye of example 17 | 0.1 g |
|---|---|---|
| | Copolymer of polyvinylpyrrolidone/ vinyl acetate, 70/30, M.W. 40,000 | 2 g |
| | Isopropyl alcohol | 40 g |
| | Triethanolamine, q.s.p. pH 8 | |
| | Water, q.s.p. | 100 g |

This composition when applied as a hair setting lotion to bleached hair imparts thereto a dark red coloration.

| a18) | Dye of example 18 | 0.12 g |
|---|---|---|
| | Terpolymer of methyl methacrylate/ stearyl methacrylate/dimethyl methacrylate - 20/23/57 (made in accordance with SN 287845 filed 11-9-1972) | 2 g |
| | Ethyl alcohol (96°) | 30 g |
| | Triethanolamine, q.s.p. pH 8.5 | |
| | Water, q.s.p. | 100 g |

This composition when applied as a hair setting lotion to bleached hair imparts thereto a cork coloration with gold glints.

| a19) | Dye of example 19 | 0.05 g |
|---|---|---|
| | vinylpyrrolidone, M.W. 40,000 | 1 g |
| | Isopropyl alcohol | 20 g |
| | Triethanolamine, q.s.p. pH 9.5 | |
| | Water, q.s.p. | 100 g |

This composition when applied as a hair setting lotion to bleached hair imparts thereto a steel-blue coloration.

| a20) | Dye of example 20 | 0.06 g |
|---|---|---|
| | Copolymer of polyvinylpyrrolidone/ vinyl acetate, 60/40, M.W. 80,000 to 120,000 | 2 g |
| | Isopropyl alcohol | 30 g |
| | Triethanolamine, q.s.p. pH 9 | |
| | Water, q.s.p. | 100 g |

This composition when applied as a hair setting lotion to bleached hair imparts thereto an ash parme coloration.

| a21) | Dye of example 21 | 0.070 g |
|---|---|---|

|      |                                                          |        |   |
|------|----------------------------------------------------------|--------|---|
|      | Copolymer of vinylpyrrolidone/                           |        |   |
|      | vinyl acetate, 30/70, M.W. 160,000                       | 2      | g |
|      | Ethyl alcohol (96°)                                      | 45     | g |
|      | Triethanolamine, q.s.p. pH 8                             |        |   |
|      | Water, q.s.p.                                            | 100    | g |

This composition when applied as a hair setting lotion to bleached hair imparts thereto a grey-green coloration.

| a22) | Dye of example 22                                        | 0.2    | g |
|------|----------------------------------------------------------|--------|---|
|      | vinylpyrrolidone, M.W. 40,000                            | 2      | g |
|      | Ethyl alcohol (96°)                                      | 40     | g |
|      | Triethanolamine, q.s.p. pH 9                             |        |   |
|      | Water, q.s.p.                                            | 100    | g |

This composition when applied as a hair setting lotion to bleached hair imparts thereto an ocean-green coloration.

| a23) | Dye of example 23                                        | 0.1    | g |
|------|----------------------------------------------------------|--------|---|
|      | Polyvinylpyrrolidone, M.W. 40,000                        | 2      | g |
|      | Ethyl alcohol (96°)                                      | 40     | g |
|      | Triethanolamine, q.s.p. pH 6                             |        |   |
|      | Water, q.s.p.                                            | 100    | g |

This composition when applied as a hair setting lotion to bleached hair imparts thereto a turquoise coloration.

| a24) | Dye of example 26                                        | 0.2    | g |
|------|----------------------------------------------------------|--------|---|
|      | Copolymer of vinylpyrrolidone/                           |        |   |
|      | vinyl acetate, 60/40, M.W. 80,000 to 120,000             | 3      | g |
|      | Ethyl alcohol (96°)                                      | 50     | g |
|      | Ammonia, q.s.p. pH 11                                    |        |   |
|      | Water, q.s.p.                                            | 100    | g |

This composition when applied as a hair setting lotion to bleached hair imparts thereto a heliotrope coloration.

| a25) | Dye of example 31                                        | 0.1    | g |
|------|----------------------------------------------------------|--------|---|
|      | Copolymer of vinyl acetate/                              |        |   |
|      | crotonic acid, 90/10, M.W. 45,000 to 50,000              | 2      | g |
|      | Ethyl alcohol (96°)                                      | 50     | g |
|      | Triethanolamine, q.s.p. pH 7                             |        |   |
|      | Water, q.s.p.                                            | 100    | g |

This composition when applied as a hair setting lotion to 95% white hair imparts thereto a very silvery glycine coloration.

| a26) | Dye of example 32                                        | 0.1    | g |
|------|----------------------------------------------------------|--------|---|
|      | Copolymer of vinyl acetate/                              |        |   |
|      | crotonic acid, 90/10, M.W. 45,000 to 50,000              | 2      | g |
|      | Ethyl alcohol (96°)                                      | 50     | g |
|      | Triethanolamine, q.s.p. pH 7                             |        |   |
|      | Water, q.s.p.                                            | 100    | g |

This solution when applied as a hair setting lotion to 95% white hair imparts thereto a pearly-beige coloration having rose glints.

| a27) | Dye of example 33                                        | 0.1    | g |
|------|----------------------------------------------------------|--------|---|
|      | Copolymer of vinyl acetate/                              |        |   |
|      | crotonic acid, 90/10, M.W. 45,000 to 50,000              | 2      | g |
|      | Ethyl alcohol (96°)                                      | 50     | g |
|      | Triethanolamine, q.s.p. pH 8                             |        |   |
|      | Water, q.s.p.                                            | 100    | g |

This composition when applied as a hair setting lotion to bleached hair imparts thereto a pink champagne coloration.

| a28) | Dye of example 34                                        | 0.3    | g |
|------|----------------------------------------------------------|--------|---|
|      | Copolymer of vinyl acetate/                              |        |   |
|      | crotonic acid, 90/10, M.W. 45,000 to 50,000              | 2      | g |
|      | Ethanol (96°)                                            | 50     | g |
|      | Triethanolamine, q.s.p. pH 7                             |        |   |
|      | Water, q.s.p.                                            | 100    | g |

This composition when applied as a hair setting lotion to bleached hair imparts thereto a beige coloration with parme glints.

| a29) | Dye of example 35                                        | 0.10   | g |
|------|----------------------------------------------------------|--------|---|
|      | Copolymer of vinylpyrrolidone/                           |        |   |
|      | vinyl acetate, 60/40, M.W. 80,000 to 120,000             | 2.3    | g |
|      | Isopropyl alcohol                                        | 30     | g |
|      | Triethanolamine, q.s.p. pH 8                             |        |   |
|      | Water, q.s.p.                                            | 100    | g |

This composition when applied as a hair setting lotion to bleached hair imparts thereto a blue-grey coloration.

| a30) | Dye of example 36                                        | 0.08   | g |
|------|----------------------------------------------------------|--------|---|
|      | vinylpyrrolidone, M.W-40,000                             | 2      | g |
|      | Isopropyl alcohol                                        | 35     | g |
|      | Triethanolamine, q.s.p. pH 9.5                           |        |   |
|      | Water, q.s.p.                                            | 100    | g |

This composition when applied as a hair setting lotion to bleached hair imparts thereto a myosotis coloration.

| a31) | Dye of example 37                                        | 0.53   | g |
|------|----------------------------------------------------------|--------|---|
|      | Copolymer of vinyl acetate/crotonic                      |        |   |
|      | acid, 90/10, M.W. 45,000 to 50,000                       | 2      | g |
|      | Ethanol (96°)                                            | 50     | g |
|      | Triethanolamine, q.s.p. pH 8.6                           |        |   |
|      | Water, q.s.p.                                            | 100.00 | g |

This composition when applied as a hair setting lotion to 95% naturally white hair imparts thereto a silver-grey coloration with mauve glints.

| a32) | Dye of example 30                                        | 0.75   | g |
|------|----------------------------------------------------------|--------|---|
|      | Copolymer of vinyl acetate/                              |        |   |
|      | crotonic acid 90/10 – M.W. 45,000 to 50,000              | 2      | g |
|      | Ethanol (96°)                                            | 50     | g |
|      | Water, q.s.p.                                            | 100    | g |
|      | Ammonia (22° Be), q.s.p. pH 10                           |        |   |

This composition when applied as a hair setting lotion to 95% naturally white hair imparts thereto a parme coloration.

| a33) | Dye of example 38                                        | 1.75   | g |
|------|----------------------------------------------------------|--------|---|
|      | Copolymer of vinyl acetate/                              |        |   |
|      | crotonic acid, 90/10, M.W. 45,000 to 50,000              | 1      | g |
|      | Ethanol (96°)                                            | 25.00  | g |
|      | Triethanolamine, q.s.p. pH 7                             |        |   |

-continued

| Water, q.s.p. | 100 | g |

This composition when applied as a hair setting lotion to bleached hair imparts thereto a very strong violet coloration.

| a34) | Dye of example 39 | 1 | g |
|---|---|---|---|
| | Copolymer of vinyl acetate/ crotonic acid, 90/10, M.W. 45,000 to 50,000 | 2 | g |
| | Ethanol (96°) | 50 | g |
| | Triethanolamine, q.s.p. pH 9 | | |
| | Water, q.s.p. | 100.0 | g |

This composition when applied as a hair setting lotion to 95% naturally white hair imparts thereto an intense emerald green coloration.

| a35) | Dye of example 40 | 0.2 | g |
|---|---|---|---|
| | Copolymer of vinyl acetate/ crotonic acid, 90/10, M.W. 45,000 to 50,000 | 2 | g |
| | Ethanol (96°) | 50 | g |
| | Water, q.s.p. | 100 | g |
| | Triethanolamine, q.s.p. pH 8.5 | | |

This composition when applied as a hair setting lotion to 95% naturally white hair imparts thereto a silvery, grey-green coloration.

| a36) | Dye of example 41 | 1 | g |
|---|---|---|---|
| | Copolymer of vinyl acetate/ crotonic acid, 90/10, M.W. - 45,000 o 50,000 | 2 | g |
| | Ethyl alcohol (96°) | 50 | g |
| | Triethanolamine, q.s.p. pH 7 | | |
| | Water, q.s.p. | 100 | g |

This composition when applied as a hair setting lotion to bleached hair imparts thereto an intense violet coloration.

| a37) | Dye of example 42 | 0.15 | g |
|---|---|---|---|
| | Copolymer of vinylpyrrolidone/ vinyl acetate, 60/40, sold under the name PVP/VAS 630 | 2 | g |
| | Isopropanol | 35 | g |
| | Triethanolamine, q.s.p. pH 9 | | |
| | Water, q.s.p. | 100 | g |

This composition when applied as a hair setting lotion to bleached hair imparts thereto a pearly lavender coloration.

| a38) | Dye of example 43 | 0.15 | g |
|---|---|---|---|
| | Copolymer of vinylpyrrolidone/ vinyl acetate, 60/40, sold under the name PVP/VAS 630 | 2 | g |
| | Isopropanol | 35 | g |
| | Lactic acid - 10% solution, q.s.p. pH 6 | | |
| | Water, q.s.p. | 100 | g |

This composition when applied as a hair setting lotion to bleached hair imparts thereto a pearly light blue coloration.

| a39) | Dye of example 44 | 0.2 | g |
|---|---|---|---|
| | Copolymer of vinylacetate/crotonic acid, 90/10, M.W. - 45,000 to 50,000 | 1 | g |
| | Ethyl alcohol (96°) | 36 | g |
| | Ammonia (22° Be), q.s.p. pH 7.5 | | |

-continued

| Water, q.s.p. | 100 | g |

This composition when applied as a hair setting lotion to bleached hair imparts thereto a metallic gray coloration with blue glints.

| a40) | Dye of Example 45 | 0.05 | g |
|---|---|---|---|
| | Copolymer of vinyl acetate/crotonic acid, 90/10, M.W. - 45,000 to 50,000 | 1 | g |
| | Ethyl alcohol (96°) | 36 | g |
| | Lactic acid - 10% solution, q.s.p. pH 5 | | |
| | Water, q.s.p. | 100 | g |

This composition when applied as a hair setting lotion to bleached hair imparts thereto a silvery gray coloration shaded mauve.

| a41) | Dye of example 46 | 0.05 | g |
|---|---|---|---|
| | Copolymer of vinylpyrrolidone/ vinyl acetate, 30/70, sold under the name PVP/VAE E 335 | 2 | g |
| | Ethyl alcohol (96°) | 40 | g |
| | Triethanolamine, q.s.p. pH 8 | | |
| | Water, q.s.p. | 100 | g |

This composition when applied as a hair setting lotion to bleached hair, imparts thereto a light gray coloration with glycine glints.

| a42) | Dye of example 47 | 0.25 | g |
|---|---|---|---|
| | Copolymer of vinyl acetate/crotonic acid, 90/10, M.W. - 45,000 to 50,000 | 2 | g |
| | Ethyl alcohol (96°) | 50 | g |
| | Ammonia (22° Be), q.s.p. pH 7.5 | | |
| | Water, q.s.p. | 100 | g |

This composition when applied as a hair setting lotion to bleached hair imparts thereto a pearly parme coloration.

| a43) | Dye of example 48 | 0.06 | g |
|---|---|---|---|
| | Copolymer of vinyl acetate/crotonic acid, 90/10, M.W. - 45,000 to 50,000 | 1 | g |
| | Ethyl alcohol (96°) | 36 | g |
| | Triethanolamine, q.s.p. pH 7.5 | | |
| | Water, q.s.p. | 100 | g |

This composition when applied as a hair setting lotion to bleached hair imparts thereto a pearly tamarisk rose coloration.

| a44) | Dye of example 49 | 0.1 | g |
|---|---|---|---|
| | Copolymer of vinylpyrrolidone/ vinyl acetate, 60/40, sold under the name PVP/VA S 630 | 2 | g |
| | Isopropanol | 35 | g |
| | Ammonia (22° Be), q.s.p. pH 9 | | |
| | Water, q.s.p. | 100 | g |

This composition when applied as a hair setting lotion to bleached hair imparts thereto an iridescent light blue grey coloration.

| a45) | Dye of example 50 | 0.2 | g |
|---|---|---|---|
| | Copolymer of vinylpyrrolidone/ vinyl acetate, 30/70, sold under the name PVP/VAE E 335 | 2 | g |
| | Ethyl alcohol (96°) | 40 | g |
| | Lactic acid - 10% solution, q.s.p. pH 5 | | |

| | | | |
|---|---|---|---|
| | -continued | | |
| | Water, q.s.p. | 100 | g |

This composition when applied as a hair setting lotion to bleached hair imparts thereto a silvery light blue coloration.

| a46) | Dye of example 51 | 0.4 | g |
|---|---|---|---|
| | Copolymer of vinylpyrrolidone/ vinyl acetate, 30/70, sold under the name PVP/VAE E 335 | 2 | g |
| | Ethyl alcohol (96°) | 40 | g |
| | Lactic acid - 10% solution, q.s.p. pH 4.5 | | |
| | Water, q.s.p. | 100 | g |

This composition when applied as a hair setting lotion to bleached hair imparts thereto a very luminous glycine coloration.

| a47) | Dye of example 51 | 0.2 | g |
|---|---|---|---|
| | N-[(4'-hydroxy) phenyl]-2-methyl-5-amino benzoquinoneimine | 0.2 | g |
| | Nitro-orthophenylenediamine | 0.5 | g |
| | Copolymer of vinylpyrrolidone/vinyl acetate 60/40 M.W. 80,000 to 120,000 | 2 | g |
| | Isopropanol | 35 | g |
| | Ammonia (22° Be) q.s.p. pH 9 | | |
| | Water q.s.p. | 100 | g |

This composition when applied as a hair setting lotion to 95% naturally white hair imparts thereto an icy chestnut coloration.

| a48) | Dye of example 51 | 0.20 | g |
|---|---|---|---|
| | 2-N,N-methyl,β-hydroxyethylamino-5-(4'-amino)-anilino -1,4-benzoquinone | 0.10 | g |
| | N-[(4'-hydroxy-2-'-chloro)phenyl[-2-methyl-5-carbethoxy benzoquinoneimine | 0.20 | g |
| | Polyvinylpyrrolidone M.W. 160,000 | 2 | g |
| | Isopropanol | 25 | g |
| | Ammonia (22° Be), q.s.p. pH 10.5 | | |
| | Water, q.s.p. | 100 | g |

This composition when applied as a hair setting lotion to bleached hair imparts thereto a beige coloration with light mordore glints.

| a49) | Dye of example 45 | 0.30 | g |
|---|---|---|---|
| | Dye of example 43 | 0.05 | g |
| | N-[(4'hydroxy)phenyl]-2-methyl-5-β-hydroxyethylamino benzoquinoneimine | 0.14 | g |
| | N-[(4'-hydroxy-2-'-methyl)phenyl]-2,6-dimethyl benzoquinoneimine | 0.06 | g |
| | Copolymer of vinyl acetate/crotonic acid, 90/10, M.W. 45,000 to 50,000 | 2 | g |
| | Ammonia (22° Be), q.s.p. pH 10 | | |
| | Ethyl alcohol (96°) q.s.p. | 40 | g |
| | Water q.s.p. | 100 | g |

This composition when applied as a hair setting lotion to 95% naturally white hair imparts thereto a steel gray coloration with mauve glints.

| a50) | Dye of example 44 | 0.30 | g |
|---|---|---|---|
| | N-[(4'-hydroxy)phenyl]-2-methyl-5-β-hydroxyethylamino benzoquinoneimine | 0.40 | g |
| | N-[(4'-hydroxy-3-'-methyl)phenyl]-2-methyl-5-acetylamino benzoquinoneimine | 0.20 | g |
| | Copolymer of vinylpyrrolidone/vinyl acetate, 30/70, sold under the name PVP/VAE E 335 | 2 | g |
| | Ethyl alcohol (96°) | 40.00 | g |
| | Ammonia (22° Be) q.s.p. pH 10.5 | | |

| | | | |
|---|---|---|---|
| | -continued | | |
| | Water, q.s.p. | 100 | g |

This composition when applied as a hair setting lotion to bleached hair imparts thereto a copper coloration with pink glints.

| a51) | Dye of example 53 | 0.20 | g |
|---|---|---|---|
| | Copolymer of vinylacetate/crotonic acid, 90/10, M.W. 45,000 to 50,000 | 2 | g |
| | Ethyl alcohol (96°) | 50 | g |
| | Ammonia (22° Be), q.s.p. pH 8 | | |
| | Water, q.s.p. | 100 | g |

This composition when applied as a hair setting lotion to bleached hair imparts thereto, an intense royal blue coloration.

| a52) | Dye of example 54 | 0.30 | g |
|---|---|---|---|
| | Copolymer of vinyl acetate/crotonic acid, 90/10, M.W. 45,000 to 50,000 | 2 | g |
| | Ethyl alcohol (96°) | 50 | g |
| | Ammonia (22° Be) q.s.p. pH 10 | | |
| | Water, q.s.p. | 100 | g |

This composition when applied as a hair setting lotion to bleached hair imparts thereto a very luminous violet-mauve coloration.

| a53) | Dye of example 55 | 0.6 | g |
|---|---|---|---|
| | Copolymer of vinyl acetate/crotonic acid, 90/10, M.W. 45,000 to 50,000 | 2 | g |
| | Ethyl alcohol (96°) | 50 | g |
| | Ammonia (22° Be), q.s.p. pH 8 | | |
| | Water, q.s.p. | 100 | g |

This composition when applied as a hair setting lotion to bleached hair imparts thereto a dark violet coloration.

Part B - Examples of Dye Compositions

| b1) | Dye of example 11 | 0.2 | g |
|---|---|---|---|
| | Ammonium lauryl sulfate | 20 | g |
| | Triethanolamine, q.s.p. pH 8.5 | | |
| | Water, q.s.p. | 100 | g |

This composition is applied to white hair for a period of 30 minutes at ambient temperature. After rinsing, shampooing, rinsing again and drying, it imparts thereto a sandlewood coloration with golden glints.

| b2) | Dye of example 2 | 0.5 | g |
|---|---|---|---|
| | Butylglycol | 5 | g |
| | Lauryl alcohol oxyethylenated with 10.5 moles of ethylene oxide | 5 | g |
| | Triethanolamine, q.s.p. pH 8 | | |
| | Water, q.s.p. | 100 | g |

This composition is applied to gray hair for a period of 30 minutes at ambient temperature. After rinsing, shampooing, rinsing again and drying, it imparts thereto a brilliant deep blue coloration.

| b3) | Dye of example 29 | 0.785 | g |
|---|---|---|---|
| | Ethyl alcohol (96°) | 30 | g |
| | Triethanolamine, q.s.p. pH 9.5 | | |
| | Water, q.s.p. | 100 | g |

This composition is applied to white hair for a period of 30 minutes at ambient temperature. After rinsing, shampooing, rinsing again and drying, it imparts thereto a French-blue coloration.

| b4) | Dye of example 25 | 0.91 | g |
|---|---|---|---|
| | Ethyl alcohol (96°) | 30 | g |
| | Triethanolamine, q.s.p. pH 9.5 | | |
| | Water, q.s.p. | 100 | g |

This composition is applied to white hair for a period of 30 minutes at ambient temperature. After rinsing, shampooing, rinsing again and drying, it imparts thereto a gazelle-beige coloration.

| b5) | Dye of example 24 | 0.92 | g |
|---|---|---|---|
| | Ethyl alcohol (96°) | 30 | g |
| | Triethanolamine, q.s.p. pH 9.5 | | |
| | Water, q.s.p. | 100 | g |

This composition is applied to white hair for a period of 30 minutes at ambient temperature. After rinsing, shampooing, rinsing again and drying, it imparts thereto a champagne coloration.

| b6) | Dye of example 30 | 0.95 | g |
|---|---|---|---|
| | Ethyl alcohol (96°) | 30 | g |
| | Triethanolamine, q.s.p. pH 9.5 | | |
| | Water, q.s.p. | 100 | g |

This composition is applied to white hair for a period of 30 minutes at ambient temperature. After rinsing, shampooing, rinsing again and drying, it imparts thereto an amethyst-blue coloration.

| b7) | Dye according to example 21 | 0.84 | g |
|---|---|---|---|
| | Ethyl alcohol (96°) | 30 | g |
| | Triethanolamine, q.s.p. pH 9.5 | | |
| | Water, q.s.p. | 100 | g |

This composition is applied to white hair for a period of 30 minutes at ambient temperature. After rinsing, shampooing, rinsing again and drying, it imparts thereto a metallic blue-green coloration.

| b8) | Dye of example 28 | 0.78 | g |
|---|---|---|---|
| | Ethyl alcohol (96°) | 30 | g |
| | Triethanolamine, q.s.p. pH 9.5 | | |
| | Water, q.s.p. | 100 | g |

This combination is applied to white hair for a period of 30 minutes at ambient temperature. After rinsing, shampooing, rinsing again and drying, it imparts thereto a pearly-grey coloration with violet glints.

| b9) | Dye of example 27 | 0.89 | g |
|---|---|---|---|
| | Ethyl alcohol (96°) | 30 | g |
| | Triethanolamine, q.s.p. pH 9.5 | | |
| | Water, q.s.p. | 100 | g |

This composition is applied to white hair for a period of 40 minutes at ambient temperature. After rinsing, shampooing, rinsing again and drying, it imparts thereto a pastel yellow-blue coloration.

| b10) | Dye of example 9 | 0.82 | g |
|---|---|---|---|
| | Ethyl alcohol (96°) | 30 | g |
| | Triethanolamine, q.s.p. pH 9.5 | | |
| | Water, q.s.p. | 100 | g |

This composition is applied to white hair for a period of 30 minutes at ambient temperature. After rinsing, shampooing, rinsing again and drying, it imparts thereto a light chestnut coloration with mauve glints.

| b11) | Dye of example 15 | 0.93 | g |
|---|---|---|---|
| | Ethyl alcohol (96°) | 30 | g |
| | Triethanolamine, q.s.p. pH 9.5 | | |
| | Water, q.s.p. | 100 | g |

This composition is applied to white hair for a period of 30 minutes at ambient temperature. After rinsing, shampooing, rinsing again and drying, it imparts thereto an ice-blue coloration.

| b12) | Dye of example 14 | 0.86 | g |
|---|---|---|---|
| | Ethyl alcohol (96°) | 30 | g |
| | Triethanolamine, q.s.p. pH 9.5 | | |
| | Water, q.s.p. | 100 | g |

This composition is applied to white hair for a period of 30 minutes at ambient temperature. After rinsing, shampooing, rinsing again and drying, it imparts thereto a duck blue coloration.

| b13) | Dye of example 16 | 0.89 | g |
|---|---|---|---|
| | Ethyl alcohol (96°) | 30 | g |
| | Triethanolamine, q.s.p. pH 9.5 | | |
| | Water, q.s.p. | 100.00 | g |

This composition is applied to white hair for a period of 30 minutes at ambient temperature. After rinsing, shampooing, rinsing again and drying, it imparts thereto a Nile green coloration.

| b14) | Dye of example 20 | 0.92 | g |
|---|---|---|---|
| | Ethyl alcohol (96°) | 30 | g |
| | Triethanolamine, q.s.p. pH 9.5 | | |
| | Water, q.s.p. | 100 | g |

This composition is applied to white hair for a period of 30 minutes at ambient temperature. After rinsing, shampooing, rinsing again and drying, it imparts thereto a cardinal violet coloration.

| b15) | Dye of example 20 | 0.92 | g |
|---|---|---|---|
| | Butylglycol | 5 | g |
| | Lauryl alcohol oxyethylenated with 10.5 moles of ethylene oxide | 5 | g |
| | Triethanolamine, q.s.p. pH 9.5 | | |
| | Water, q.s.p. | 100 | g |

This composition is applied to white hair for a period of 30 minutes at ambient temperature. After rinsing, shampooing, rinsing again and drying, it imparts thereto a lilac coloration.

| b16) | Dye of example 17 | 0.95 | g |
|---|---|---|---|
| | Butylglycol | 5 | g |
| | Lauryl alcohol oxyethylenated with 10.5 moles of ethylene oxide | 5 | g |
| | Triethanolamine, q.s.p. pH 9.5 | | |
| | Water, q.s.p. | 100 | g |

This composition is applied to white hair for a period of 30 minutes at ambient temperature. After rinsing, shampooing, rinsing again and drying, it imparts thereto a plum coloration.

| b17) | Dye of example 26 | 0.98 g |
|---|---|---|
| | Ammonia, q.s.p. pH 9 | |
| | Water, q.s.p. | 100 g |

This composition is applied to bleached hair for a period of 20 minutes at ambient temperature. After rinsing, shampooing, rinsing again and drying, it imparts thereto a silver-grey coloration with violet glints.

| b18) | Dye of example 23 | 0.94 |
|---|---|---|
| | Ethyl alcohol (96°) | 30 g |
| | Ammonia, q.s.p. pH 10 | |
| | Water, q.s.p. | 100 g |

This composition is applied to bleached hair for a period of 15 minutes at ambient temperature. After rinsing, shampooing, rinsing again and drying, it imparts thereto a pastel golden green coloration.

| b19) | Dye of Example 23 - Gel Composition | 0.94 g |
|---|---|---|
| | Nonylphenol oxyethylenated with 9 moles of ethylene oxide | 12.5 g |
| | Diethanolamide of fatty acid of coco and coprah | 6.25 g |
| | Butylglycol | 3.1 g |
| | Propylene glycol | 10 g |
| | Ammonia, q.s.p. pH 10 | |
| | Water, q.s.p. | 100 g |

This composition is applied to white hair and is permitted to remain in contact therewith for a period of 20 minutes. After rinsing, shampooing, rinsing again and drying, it imparts thereto a brilliant sea-green coloration.

| b20) | Dye of example 17 | 0.95 g |
|---|---|---|
| | Ethyl alcohol (96°) | 30 g |
| | Triethanolamine, q.s.p. pH 9.5 | |
| | Water, q.s.p. | 100 g |

This composition is applied to white hair for a period of 30 minutes at ambient temperature. After rinsing, shampooing, rinsing again and drying, it imparts thereto an eggplant coloration.

| b21) | Dye of example 41 | 1 g |
|---|---|---|
| | Diethanolamides of fatty acids of coprah | 10 g |
| | Ammonia (22° Be), q.s.p. pH 9 | |
| | Water, q.s.p. | 100 g |

This dye composition is applied for a period of 20 minutes at 25° C to 95% naturally white hair and after rinsing, shampooing, and rinsing again imparts thereto a metallic blue gray coloration.

| B22) | Dye of example 42 | 0.1 g |
|---|---|---|
| | Sodium lauryl sulfate wherein 19% of the starting alcohol is oxyethylenated | 20 g |
| | Ethylene diamine tetraacetic acid- "TRILON B" | 0.2 g |
| | Ammonia (22° Be) pH 10.5 | |
| | Water, q.s.p. | 100 g |

This dye composition is applied for 25 minutes at 35° C to bleached hair and after rinsing, shampooing and rinsing again imparts thereto an ice-blue coloration.

| b23) | Dye of example 43 | 0.7 g |
|---|---|---|
| | Nonylphenol oxyethylenated with 4 moles of ethylene oxide | 10 g |
| | Nonylphenol oxyethylenated with 9 moles of ethylene oxide | 10 g |
| | Water, q.s.p. | 100 g |
| | Ammonia (22° Be), q.s.p. pH 9.5 | |

This dye composition is applied for 20 minutes at 30° C to bleached hair and after rinsing, shampooing and rinsing again imparts thereto a sea-green coloration.

| b24) | Dye of example 44 | 0.26 g |
|---|---|---|
| | Nonylphenol oxyethylenated with 9 moles of ethylene oxide | 12 g |
| | Diethanolamides of the fatty acids of coprah | 6 g |
| | Butylglycol | 3 g |
| | Propylene glycol | 10 g |
| | Ammonia (22° Be), q.s.p. pH 10 | |
| | Water, q.s.p. | 100 g |

This dye composition is applied for a period of 25 minutes at 30° C to bleached hair and imparts thereto a silvery myosotis coloration.

| b25) | Dye of example 45 | 0.1 g |
|---|---|---|
| | Ammonium lauryl sulphate | 10 g |
| | Ammonia (22° Be), q.s.p. pH 10 | |
| | Water, q.s.p. | 100 g |

This dye composition is applied for a period of 25 minutes at 35° C to bleached hair and after rinsing, shampooing and rinsing again, imparts thereto a very silvery light-blue coloration.

| b26) | Dye of example 46 | 0.15 g |
|---|---|---|
| | Butylglycol | 5 g |
| | Lauryl alcohol oxyethylenated with 10.5 moles of ethylene oxide | 5 g |
| | Ammonia (22° Be), q.s.p. pH 9.5 | |
| | Water, q.s.p. | 100.00 g |

This dye composition is applied for a period of 20 minutes at 25° C to bleached hair and after rinsing, shampooing and rinsing again, imparts thereto a light silver coloration with blue glints.

| b27) | Dye of example 47 | 0.25 g |
|---|---|---|
| | Monomethyl ester of diethylene glycol | 10 g |
| | Ammonia (22° Be), q.s.p. pH 11 | |
| | Water, q.s.p. | 100 g |

This dye composition is applied for a period of 30 minutes at 30° C to bleached hair and after rinsing, shampooing and rinsing again, imparts thereto a pearly very light mauve coloration.

| b28) | Dye of example 50 | 0.4 g |
|---|---|---|
| | Ethyl alcohol (96°) | 20 g |
| | Carboxymethylcellulose | 4 g |
| | Lactic acid (10% solution) q.s.p. pH 6 | |

| | | |
|---|---|---|
| Water, q.s.p. | 100 | g |

This dye composition is applied for a period of 20 minutes at 35° C to bleached hair and after rinsing, shampooing and rinsing again, imparts thereto a pearly light horizon-blue coloration.

| b29) | Dye of example 51 | 0.5 | g |
|---|---|---|---|
| | Ethyl alcohol (96°) | 17 | g |
| | Crosslinked polyacrylic acid - CARBOPOL 934 - polymer of acrylic acid - M.W. $2 \times 10^6 - 3 \times 10^6$ | 3.7 | g |
| | Ammonia (22° Be), q.s.p. pH 8 | | |
| | Water, q.s.p. | 100 | g |

This dye composition is applied for a period of 30 minutes at ambient temperature to bleached hair and imparts thereto, after rinsing, shampooing, and rinsing again, a very light beige coloration with blue highlights.

| b30) | Dye of example 52 | 0.05 | g |
|---|---|---|---|
| | Lauryl alcohol oxyethylenated with 10.5 moles of ethylene oxide | 20 | g |
| | Triethanolamine, q.s.p. pH 6 | | |
| | Water, q.s.p. | 100 | g |

This dye composition is applied for a period of 20 minutes at 25° C to bleached hair and after rinsing, shampooing, and rinsing again, imparts thereto a pearly light parme coloration.

Part C - Dye Compositions Containing Indoanilines of Formula (I) and other dyes

| c1) | Dye of example 1 | 0.3 | g |
|---|---|---|---|
| | Hydrobromide of 2-nitro-4-N($\beta$-aminoethyl)amino aniline | 0.1 | g |
| | Butylglycol | 5 | g |
| | Lauryl alcohol oxyethylenated with 10 moles of ethylene oxide | 5 | g |
| | Triethanolamine, q.s.p. pH 9.2 | | |
| | Water, q.s.p. | 100 | g |

This composition is applied to white hair for a period of 30 minutes at ambient temperature. After rinsing, shampooing, rinsing again and drying, it imparts thereto a rosewood coloration.

| c2) | Dye of example 2 | 0.25 | g |
|---|---|---|---|
| | 1,5-[di-N,N'-[($\beta$-methylmorpholinium) ethyl] amino anthraquinone]dimethosulfate | 0.25 | g |
| | Butylglycol | 5 | g |
| | Lauryl alcohol oxyethylenated with 10 moles of ethylene oxide | 5 | g |
| | Triethanolamine, q.s.p. pH 8.6 | | |
| | Water, q.s.p. | 100 | g |

This composition is applied to white hair for a period of 30 minutes at ambient temperature. After rinsing, shampooing, rinsing again and drying, it imparts thereto an egg-plant coloration.

| c3) | Dye of example 29 | 0.1 | g |
|---|---|---|---|
| | N-[(4'-hydroxy-3'-chloro) phenyl]-2-methyl-5-methylamino benzoquinoneimine | 0.1 | g |
| | N-[(4'-amino-2'-methoxy-5'-methyl) phenyl]-3-ureido benzoquinoneimine | 0.1 | g |
| | Di-1,4-N,N'-($\beta$-morpholinoethyl)amino anthraquinone | 0.1 | g |
| | Dihydrochloride of 2-nitro-4-N-(diethylaminoethyl) amino aniline | 0.1 | g |
| | 2-amino-4,4-dihydroxy azobenzene | 0.1 | g |
| | Butylglycol | 5 | g |
| | Monoethanolamine, q.s.p. pH 6 | | |
| | Water q.s.p. | 100 | g |

This composition is applied to white hair and is permitted to remain in contact therewith for 10 minutes. After rinsing, shampooing, rinsing again and drying, it imparts thereto a fir-green coloration.

| c4) | N-[(4'-hydroxy-2'-chloro) phenyl]-2,5-diacetylamino benzoquinoneimine | 0.1 | g |
|---|---|---|---|
| | N-[(4'-amino-2',5'-dimethyl)phenyl]-2-ureido benzoquinoneimine | 0.1 | g |
| | [1,5-N,N'-[($\beta$-methylmorpholinium) ethyl] amino anthraquinone] dimethosulfate | 0.1 | g |
| | Hydrobromide of 2-nitro-4-N-($\beta$-aminoethyl) amino aniline | 0.1 | g |
| | 2-amino-4,4'-dihydroxy azobenzene | 0.1 | g |
| | Butylglycol | 5 | g |
| | Ammonia, q.s.p. pH 10 | | |
| | Water, q.s.p. | 100 | g |

This composition is applied to bleached hair for a period of 10 minutes. After rinsing, shampooing, rinsing again and drying, it imparts thereto a squirrel coloration.

| c5) | N-[[4'-(ethyl, piperidinoethyl) amino]phenyl]-2,6-dimethyl-3-amino benzoquinoneimine, monohydrochloride, monohydrate | 0.02 | g |
|---|---|---|---|
| | N-[4'-(dimethylamino) phenyl]-3-acetylamino benzoquinoneimine N', N'-dimethyliminium chloride | 0.02 | g |
| | 5,6-dihydroxy indole | 0.01 | g |
| | Butylglycol | 5 | g |
| | Lauryl alcohol oxyethylenated with 10.5 moles of ethylene oxide | 5 | g |
| | Ammonia, q.s.p. pH 10 | | |
| | Water, q.s.p. | 100 | g |

This composition is applied to previously bleached hair for a period of 30 minutes at ambient temperature. The hair is then rinsed, washed, rinsed again and dried. The hair exhibits an ash parme coloration.

What is claimed is:

1. An indoaniline having the formula

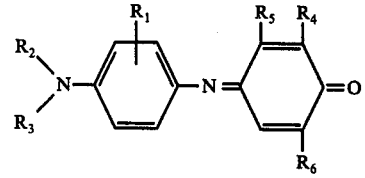

wherein:
$R_1$ represents hydrogen, halogen, alkyl or alkoxy;
$R_2$ represents alkyl and hydroxyalkyl,
$R_3$ represents piperidinoalkyl, morpholinoalkyl or $R_2$ and $R_3$ together with the nitrogen atom to which they are attached form a heterocycle selected from piperidino and morpholino;
$R_4$, $R_5$ and $R_6$ each independently represent hydrogen, halogen, alkyl, alkoxy, acetylamino, ureido or carbalkoxyamino,
with the proviso that at least one of $R_4$, $R_5$ and $R_6$ is other than hydrogen or halogen and that at least two of said $R_4$, $R_5$ and $R_6$ are other than hydrogen when $R_4$ or $R_6$ is methyl and $R_5$ can further represent amino, alkylamino, hydroxyalkylamino and carbamylalkylamino, wherein the alkyl and alkoxy groups contain from 1 to 6 carbon atoms.

2. The indoaniline of claim 1 which is N-[(4'-ethyl, β-piperidinoethylamino)phenyl]-2,6-dimethyl-3-acetylamino benzoquinoneimine.

3. The indoaniline of claim 1 which is N-[(4'-ethyl, β-piperidinoethylamino)phenyl]-2,6-dimethyl-3-amino benzoquinoneimine.

4. The indoaniline of claim 1 which is N-[(4'-ethyl, β-morpholinoethylamino)phenyl]-2-methyl-5-amino benzoquinoneimine.

5. The indoaniline of claim 1 which is N-[(4'-ethyl, β-morpholinoethylamino)phenyl]-2,6-dimethyl-3-amino benzoquinoneimine.

6. The indoaniline of claim 1 which is N-[(4'-morpholino)phenyl]-2-methyl-5-amino benzoquinoneimine.

7. The indoaniline of claim 1 which is N-[(4'-morpholino)phenyl]-2,6-dimethyl-3-amino benzoquinoneimine.

8. The indoaniline of claim 1 which is N-[(4'-piperidino)phenyl]-2-methyl-5-amino benzoquinoneimine.

9. The indoaniline of claim 1 which is N-[(4'-ethyl, β-piperidinoethylamino)phenyl]-3-chloro-6-acetylamino benzoquinoneimine.

10. The indoaniline of claim 1 which is N-[(4'-morpholino)phenyl]-2-chloro-5-acetylamino benzoquinoneimine.

* * * * *